(12) United States Patent
Sauerberg

(10) Patent No.: US 7,943,612 B2
(45) Date of Patent: May 17, 2011

(54) COMPOUNDS THAT MODULATE PPAR ACTIVITY, THEIR PREPARATION AND USE

(75) Inventor: Per Sauerberg, Farum (DK)

(73) Assignee: High Point Pharmaceuticals, LLC, High Point, NC (US)

( * ) Notice: Subject to any disclaimer, the term of this patent is extended or adjusted under 35 U.S.C. 154(b) by 155 days.

(21) Appl. No.: 12/282,244

(22) PCT Filed: Mar. 7, 2007

(86) PCT No.: PCT/EP2007/052130
§ 371 (c)(1),
(2), (4) Date: Sep. 9, 2008

(87) PCT Pub. No.: WO2007/101864
PCT Pub. Date: Sep. 13, 2007

(65) Prior Publication Data
US 2009/0048257 A1 Feb. 19, 2009

(30) Foreign Application Priority Data
Mar. 9, 2006 (EP) .................................. 06110887

(51) Int. Cl.
*A61K 31/56* (2006.01)
*C07D 295/18* (2006.01)
(52) U.S. Cl. .................................... 514/239.2; 544/171
(58) Field of Classification Search .................. 544/171; 514/239.2
See application file for complete search history.

(56) References Cited

U.S. PATENT DOCUMENTS

| | | | |
|---|---|---|---|
| 4,920,132 | A | 4/1990 | Huang et al. |
| 5,324,743 | A | 6/1994 | Dillard et al. |
| 5,538,768 | A | 7/1996 | Marden et al. |
| 6,448,293 | B1 | 9/2002 | Andrews et al. |
| 6,525,094 | B1 | 2/2003 | Zhang et al. |
| 6,630,504 | B2 | 10/2003 | Andrews et al. |
| 6,869,975 | B2 | 3/2005 | Abe et al. |
| 6,875,780 | B2 | 4/2005 | Auerbach et al. |
| 6,939,875 | B2 | 9/2005 | Auerbach et al. |
| 6,964,983 | B2 | 11/2005 | Auerbach et al. |
| 7,244,763 | B2 | 7/2007 | Bratton et al. |
| 7,816,385 | B2 | 10/2010 | Sauerberg et al. |
| 2004/0192743 | A1 | 9/2004 | Mjalli et al. |
| 2004/0209936 | A1 | 10/2004 | Bratton et al. |
| 2005/0113440 | A1 | 5/2005 | Auerbach et al. |
| 2007/0082907 | A1 | 4/2007 | Canada et al. |
| 2009/0192162 | A1 | 7/2009 | Ebdrup |
| 2009/0209588 | A1 | 8/2009 | Havranek et al. |

FOREIGN PATENT DOCUMENTS

| | | |
|---|---|---|
| GB | 2279659 | 1/1995 |
| JP | 2003/171275 | 6/2003 |
| WO | WO 97/27847 | 8/1997 |
| WO | WO 97/27857 | 8/1997 |
| WO | WO 97/28115 | 8/1997 |
| WO | WO 97/28137 | 8/1997 |
| WO | WO 97/28149 | 8/1997 |
| WO | WO 98/27974 | 7/1998 |
| WO | WO 99/04815 | 2/1999 |
| WO | WO 99/20275 | 4/1999 |
| WO | WO 01/00603 | 1/2001 |
| WO | WO 01/25181 | 4/2001 |
| WO | WO 01/25226 | 4/2001 |
| WO | WO 01/34137 | 5/2001 |
| WO | WO 01/34200 | 5/2001 |
| WO | WO 01/60807 | 8/2001 |
| WO | WO 01/66098 | 9/2001 |
| WO | WO 01/79197 | 10/2001 |
| WO | WO 02/14291 | 2/2002 |
| WO | WO 02/28434 | 4/2002 |
| WO | WO 02/46154 | 6/2002 |
| WO | WO 02/50048 | 6/2002 |
| WO | WO 02/053547 | 7/2002 |
| WO | WO 02/059098 | 8/2002 |
| WO | WO 02/062774 | 8/2002 |
| WO | WO 02/070011 | 9/2002 |
| WO | WO 02/076957 | 10/2002 |
| WO | WO 02/079162 | 10/2002 |
| WO | WO 02/080899 | 10/2002 |
| WO | WO 02/098840 | 12/2002 |
| WO | WO 02/100812 | 12/2002 |
| WO | WO 03/002081 | 1/2003 |
| WO | WO 03/016265 | 2/2003 |
| WO | WO 03/016291 | 2/2003 |
| WO | WO 03/024395 | 3/2003 |
| WO | WO 03/033453 | * 4/2003 |
| WO | WO 03/033493 | 4/2003 |
| WO | WO 03/035603 | 5/2003 |
| WO | WO 03/072100 | 9/2003 |
| WO | WO 03/074050 | 9/2003 |
| WO | WO 03/074051 | 9/2003 |

(Continued)

OTHER PUBLICATIONS

Landreth et al. Neurobiology of Aging, 2001, 22, 937-944.* Peters et al. Biochimica et Biophysica Acta 2009, 1796, 230-241.*
Golub et al., Science, vol. 286, Oct. 15, 1999, pp. 531-537.*
Epple et al. Bioorganic & Medicinal Chemistry Letters 2006, 16, 4376-4380.*
Gross et al. Best Practice & Research Clinical Endocrinology & Metabolism 2007, 21, 687-710.*
Colagiuri et al. American Journal of Public Health, Sep. 2006, vol. 96, No. 9, pp. 1562-1569.*
Park Diabetes Research and Clinical Practice 66S (2004), S33-S35.*
Curtis et al. The Journal of the American Board of Family Practice, vol. 18, pp. 37-43, (2005).*
Hussain et al. Diabetes Research and Clinical Practice 2007, 76, 317-326.*
Giron, D. J. Therm. Anal. Cal. 2001, 64, pp. 37-60.*
Giron, D. J. Therm. Anal. Cal. 2002, 68, pp. 335-357.*
B. Rodriquez-Spong et al. Advanced Drug Delivery Reviews, 2004, 56, pp. 241-274.*
Souillac, et al., Characterization of Delivery Systems, Differential Scanning Calorimetry, pp. 217-218 (in Encyclopedia of Controlled Drug Delivery, 1999, John Wiley & Sons, pp. 212-227).*

(Continued)

*Primary Examiner* — Rebecca L Anderson
(74) *Attorney, Agent, or Firm* — Robert S. Dailey

(57) ABSTRACT

Novel compounds of the general formula (I), the use of these compounds as pharmaceutical compositions, pharmaceutical compositions comprising the compounds and methods of treatment employing these compounds and compositions. The present compounds are activators of PPARδ and should be useful for treating conditions mediated by the same.

14 Claims, No Drawings

FOREIGN PATENT DOCUMENTS

| WO | WO 03/074052 | 9/2003 |
| --- | --- | --- |
| WO | WO 03/074495 | 9/2003 |
| WO | WO 03/084916 | 10/2003 |
| WO | WO 03/097607 | 11/2003 |
| WO | WO 2004/000315 | 12/2003 |
| WO | WO 2004/000762 | 12/2003 |
| WO | WO 2004/005253 | 1/2004 |
| WO | WO 2004/007439 | 1/2004 |
| WO | WO 2004/056740 | 7/2004 |
| WO | WO 2004/060871 | 7/2004 |
| WO | WO 2004/063165 | 7/2004 |
| WO | WO 2004/063166 | 7/2004 |
| WO | WO 2004/071447 | 8/2004 |
| WO | WO 2004/073606 | 9/2004 |
| WO | WO 2004/080943 | 9/2004 |
| WO | WO 2004/080947 | 9/2004 |
| WO | WO 2004/092117 | 10/2004 |
| WO | WO 2004/093879 | 11/2004 |
| WO | WO 2004/099170 | 11/2004 |
| WO | WO 2005/054176 | 6/2005 |
| WO | WO 2005/097098 | 10/2005 |
| WO | WO 2005/097762 | 10/2005 |
| WO | WO 2005/097763 | 10/2005 |
| WO | WO 2005/105726 | 11/2005 |
| WO | WO 2005/113506 | 12/2005 |
| WO | WO 2007/003581 | 1/2007 |

OTHER PUBLICATIONS

PCT International Search Report for Application No. PCT/EP2007/052130 dated Mar. 8, 2007.
Berger et al., Journal of Biological Chemistry, vol. 274, No. 10, pp. 6718-6725 (1999).
Berger, J. and Wagner, J., "Physiological and Therapeutic Roles of Peroxisome Proliferator-Activated Receptors," Diabetes Technology & Therapeutics, vol. 4(2), pp. 163-174 (2002).
Byrn et al., "Solid-State Chemistry of Drugs" SSI, Inc., Chapter 11, 2nd Edition, pp. 233-248, (1999).
Chilonczyk et al., "Hypolipidaemic and antiplatelet agents", 2001, Expert Opin. Ther. Patents, 11 (8), pp. 1301-1327.
Dressel, U. et al., Mol Endocrinol, 2003, vol. 17, Part 12, pp. 2477-2493.
Everett, L., et al., "The role of hepatic peroxisome proliferator-activated receptors (PPARs) in health and disease," Liver, vol. 20, pp. 191-199 (2000).
Fruchart, J., "PPAR and Cardiovascular Risk: Overview," J. Cardiovasc. Risk, vol. 8(4), pp. 185-186 (Aug. 2001).
Guillory, "Generation of Polymorphs, Hydrates, Solvates, and Amorphous Solids" in Polymorphism in Pharmaceutical Solids, pp. 183-226 (H. G. Brittain, ed., 1999).
Havranek et al., "E/Z Isomerization of 3,3-disubstituted allylic thioethers" Tetrahedron Lett., vol. 48, pp. 6970-6973 (2007).
Holst, D. et al., Biochem Biophys Acta, 2003, vol. 1633, pp. 43-50.
Jones, B., "Peroxisome Proliferative-Activated Receptor (PPAR) Modulators: Diabetes and Beyond," Medicinal Research Reviews, vol. 21(6), pp. 540-552 (Nov. 2001).
Kaplan, F., et al., "PPARs, Insulin Resistance and Type 2 Diabetes," J. Cardiovasc. Risk, vol. 8(4), pp. 211-217 (Aug. 2001).
Kersten, S., et al., "Roles of PPARs in health and disease," Nature, vol. 405, pp. 421-424 (May 2000).
Lee, C.H. et al., "PPAR-delta regulates glucose metabolism and insulin sensitivity", Proceedings of the National Academy of Sciences of the USA, 2006, vol. 103, No. 9, pp. 3444-3449.
Lee, C-H et al., Science, 2003, vol. 32, pp. 453-457.
Leibowitz et al., FEBS Letters, vol. 473, pp. 333-336 (2000).
Liu, K., et al., "Identification of a Series of PPAR gamma/delta Dual Agonists via Solid-Phase Parallel Synthesis," Bioorg. Med. Chem. Lett., vol. 11, pp. 2959-2962 (Nov. 2001).
Luquet, S. et al., Faseb J, 2003, vol. 17, Part 13, pp. 209-226.
Michalik, L., and Wahli, W., "Peroxisome proliferator-activated receptors: three isotypes for a multitude of functions," Curr. Opin. Biotechnology, vol. 10, pp. 564-570 (1999).
Miller, A., and Etgen, G., "Novel peroxisome proliferator-activated receptor ligands for type 2 diabetes and the metabolic syndrome," Expert Opin. Investig. Drugs, vol. 12(9), pp. 1489-1500 (2003).
Mital, A., "PPARs: Nuclear Receptors for Antidiabetics," CRIPS, vol. 3(1), pp. 5-8 (Jan.-Mar. 2002).
Muoio et al., Journal of Biological Chemistry, vol. 277, No. 29, pp. 26089-26097 (2002).
Notice of Allowance for U.S. Appl. No. 11/579,712, dated Dec. 10, 2010.
Notice of Allowance for U.S. Appl. No. 11/917,811, dated Jan. 5, 2011.
Oliver, et al., Proceedings of the National Academy of Sciences of the USA, vol. 98, 5306-5311 (2001).
Pending Claims for U.S. Appl. No. 11/579,712, dated Nov. 15, 2010.
Pending Claims for U.S. Appl. No. 11/917,811 dated May 28, 2010.
Pending Claims for U.S. Appl. No. 12/958,237, dated Dec. 1, 2010.
Sauerberg et al., Identification and Synthesis of a Novel Selective Partial PPAR-delta Agonist with Full Efficacy on Lipid Metabolism In Vitro and In Vivo J. Med. Chem., vol. 50, pp. 1495-1503 (2007).
Schiffrin et al., "Peroxisome Proliferator-Activated Receptors: Vascular and Cardiac Effects in Hypertension", Hypertension, 2003, 42; pp. 664-668.
Tanaka, T. et al., PNAS, 2003, vol. 100, Part 26, pp. 15924-15929.
Tiikkainen, M., et al., "Effects of Rosiglitazone and Metformin on Liver Fat Content, Hepatic Insulin Resistance, Insulin Clearance, and Gene Expression in Adipose Tissue in Patients with Type 2 Diabetes," Diabetes, vol. 53, pp. 2169-2176 (Aug. 2004).
Torra, I., et al., "Peroxisome proliferator-activated receptors: from transcriptional control to clinical practice," Curr. Opin. Lipidol., vol. 12, p. 245-254 (2001).
Vamecq, J. and Latruffe, N., "Medical significance of peroxisome proliferator-activated receptors," The Lancet, vol. 354, pp. 141-148 (Jul. 10, 1999).
Wahli, W., "Peroxisome Proliferator-Activated Receptors (PPARs): from metabolic control to epidermal wound healing," Swiss Med. Weekly, vol. 132, pp. 83-91 (2002).
Wang et al., "Peroxisome-proliferator-activated receptor delta activates fat metabolism to prevent obesity" Cell, vol. 113, pp. 159-170 (2003).
Wilson et al., "The PPARs: From Orphan Receptors to Drug Discovery" J. Med. Chem., vol. 43(4), pp. 527-550 (2000).

* cited by examiner

COMPOUNDS THAT MODULATE PPAR ACTIVITY, THEIR PREPARATION AND USE

CROSS-REFERENCE TO RELATED APPLICATIONS

This application is the United States national stage application, pursuant to 35 U.S.C. 371, of PCT/EP2007/052130, filed Mar. 7, 2007 which claims the benefit of European Patent Application No. 06110887.4, filed Mar. 9, 2006.

FIELD OF THE INVENTION

The present invention relates to novel compounds, to the use of these compounds as pharmaceutical compositions, to pharmaceutical compositions comprising the compounds and to a method of treatment employing these compounds and compositions. The compounds are activators of peroxisome proliferator-activated receptors (PPAR)-δ.

BACKGROUND OF THE INVENTION

Coronary artery disease (CAD) is the major cause of death in Type 2 diabetic and metabolic syndrome patients (i.e. patients that fall within the 'deadly quartet' category of impaired glucose tolerance, insulin resistance, hypertriglyceridaemia and/or obesity).

The hypolipidaemic fibrates and antidiabetic thiazolidinediones separately display moderately effective triglyceride-lowering activities although they are neither potent nor efficacious enough to be a single therapy of choice for the dyslipidaemia often observed in Type 2 diabetic or metabolic syndrome patients. The thiazolidinediones also potently lower circulating glucose levels of Type 2 diabetic animal models and humans. However, the fibrate class of compounds are without beneficial effects on glycaemia. Studies on the molecular actions of these compounds indicate that thiazolidinediones and fibrates exert their action by activating distinct transcription factors of the peroxisome proliferator activated receptor (PPAR) family, resulting in increased and decreased expression of specific enzymes and apolipoproteins respectively, both key-players in regulation of plasma triglyceride content.

PPARδ activation was initially reported not to be involved in modulation of glucose or triglyceride levels. (Berger et al., j. Biol. Chem., 1999, Vol 274, pp. 6718-6725). Later it has been shown that PPARδ activation leads to increased levels of HDL cholesterol in db/db mice (Leibowitz et al. FEBS letters 2000, 473, 333-336). Further, a PPARδ agonist when dosed to insulin-resistant middle-aged obese rhesus monkeys caused a dramitic dose-dependent rise in serum HDL cholesterol while lowering the levels of small dense LDL, fasting triglycerides and fasting insulin (Oliver et al. PNAS 2001, 98, 5306-5311). The same paper also showed that PPARδ activation increased the reverse cholesterol transporter ATP-binding cassette A1 and induced apolipoprotein A1-specific cholesterol efflux. The involvement of PPARδ in fatty acid oxidation in muscles was further substantiated in PPARU knock-out mice. Muoio et al. (J. Biol. Chem. 2002, 277, 26089-26097) showed that the high levels of PPARδ in skeletal muscle can compensate for deficiency in PPARα. Taken together these observations suggest that PPARδ activation is useful in the treatment and prevention of cardiovascular diseases and conditions including atherosclerosis, hypertriglyceridemia, and mixed dyslipidaemia (WO 01/00603).

A number of PPARδ compounds have been reported to be useful in the treatment of hyperglycemia, hyperlipidemia and hypercholesterolemia (WO 02/59098, WO 01/603, WO 01/25181, WO 02/14291, WO 01/79197, WO 99/4815, WO 97/28149, WO 98/27974, WO 97/28115, WO 97/27857, WO 97/28137, WO 97/27847 WO 2004093879, WO 2004092117, WO 2004080947, WO 2004080943, WO 2004073606, WO 2004063166, WO 2004063165, WO 2003072100, WO 2004060871, WO 2004005253, WO 2003097607, WO 2003035603, WO 2004000315, WO 2004000762, WO 2003074495, WO 2002070011, WO 2003084916, US 20040209936, WO 2003074050, WO 2003074051, WO 2003074052, JP 2003171275, WO 2003033493, WO 2003016291, WO 2002076957, WO 2002046154, WO 2002014291, WO 2001079197, WO 2003024395, WO 2002059098, WO 2002062774, WO 2002050048, WO 2002028434, WO 2001000603, WO 2001060807, WO 9728149, WO 2001034200, WO 9904815, WO 200125226, WO 2005097098, WO 2005097762, and WO 2005097763.

Glucose lowering as a single approach does not overcome the macrovascular complications associated with Type 2 diabetes and metabolic syndrome. Novel treatments of Type 2 diabetes and metabolic syndrome must therefore aim at lowering both the overt hypertriglyceridaemia associated with these syndromes as well as alleviation of hyperglycaemia. This indicate that research for compounds displaying various degree of PPARδ activation should lead to the discovery of efficacious triglyceride and/or cholesterol and/or glucose lowering drugs that have great potential in the treatment of diseases such as type 2 diabetes, dyslipidemia, syndrome X (including the metabolic syndrome, i.e. impaired glucose tolerance, insulin resistance, hypertrigyceridaemia and/or obesity), cardiovascular diseases (including atherosclerosis) and hypercholesteremia.

DEFINITIONS

All references described herein are incorporated in there entirety by reference.

"Substituted" signifies that one or more hydrogen atoms are replaced by the designated substituent. Only pharmaceutically stable compounds are intended to be covered.

When examples of definitions are provided, the definition is not meant to be limited to the specific examples.

The present invention includes all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When O or S is listed as a substituent, oxo and sulfo, respectively, it is intended that a carbon atom be replaced by either the O or S. For example if alkyl were substituted by 0 then an ether would be formed. Preferably heteroatom-heteroatom bonds such as O—O, O—S, O—N, S—S, and S—N are not formed.

The term "$C_{1-6}$-alkyl" as used herein, alone or in combination, represent a linear or branched, saturated hydrocarbon chain having the indicated number of carbon atoms. Representative examples include, but are not limited to methyl, ethyl, n-propyl, isopropyl, butyl, isobutyl, sec-butyl, tert-butyl, pentyl, isopentyl, hexyl, isohexyl and the like.

The term "$C_{1-6}$-alkylcarbonyl as used herein, represents a "$C_{1-6}$-alkyl" group as defined above having the indicated number of carbon atoms linked through a carbonyl group. Representative examples include, but are not limited to, methylcarbonyl, ethylcarbonyl, n-propylcarbonyl, isopropylcarbonyl, butylcarbonyl, isobutylcarbonyl, sec-butylcarbonyl, tert-butylcarbonyl, n-pentylcarbonyl, isopentylcarbonyl, neopentylcarbonyl, tert-pentylcarbonyl, n-hexylcarbonyl, isohexylcarbonyl and the like.

The term "$C_{1-6}$-alkylsulfonyl" as used herein refers to a monovalent substituent comprising a "$C_{1-6}$-alkyl" group as defined above linked through a sulfonyl group. Representative examples include, but are not limited to, methylsulfonyl, ethylsulfonyl, n-propylsulfonyl, iso-propylsulfonyl, n-butylsulfonyl, isobutylsulfonyl, sec-butylsulfonyl, tert-butylsulfonyl, n-pentyl-sulfonyl, isopentylsulfonyl, neopentylsulfonyl, tert-pentylsulfonyl, n-hexylsulfonyl, isohexylsulfonyl and the like.

The term "$C_{1-6}$-alkylamido" as used herein, refers to an acyl group linked through an amino group; Representative examples include, but are not limited to acetylamino, propionylamino, butyrylamino, isobutyrylamino, pivaloylamino, valerylamino and the like.

The term "$C_{3-6}$-cycloalkyl" as used herein, alone or in combination, represent a saturated monocyclic hydrocarbon group having the indicated number of carbon atoms. Representative examples include, but are not limited to cyclopropyl, cyclobutyl, cyclopentyl, cyclohexyl and the like.

The term "$C_{2-6}$-alkenyl" as used herein, represent an olefinically unsaturated branched or straight hydrocarbon group having from 2 to the specified number of carbon atoms and at least one double bond. Representative examples include, but are not limited to, vinyl, 1-propenyl, 2-propenyl, allyl, isopropenyl, 1,3-butadienyl, 1-butenyl, hexenyl, pentenyl and the like.

The term "$C_{2-6}$-alkynyl" as used herein, represent an unsaturated branched or straight hydrocarbon group having from 2 to the specified number of carbon atoms and at least one triple bond. Representative examples include, but are not limited to, 1-propynyl, 2-propynyl, 1-butynyl, 2-butynyl, 1-pentynyl, 2-pentynyl and the like.

The term "$C_{4-6}$-alkenynyl" as used herein, represent an unsaturated branched or straight hydrocarbon group having from 4 to the specified number of carbon atoms and both at least one double bond and at least one triple bond. Representative examples include, but are not limited to, 1-penten-4-ynyl, 3-penten-1-ynyl, 1,3-hexadiene-5-ynyl and the like.

The term "$C_{1-6}$-alkoxy" as used herein, alone or in combination, refers to a straight or branched configuration linked through an ether oxygen having its free valence bond from the ether oxygen. Examples of linear alkoxy groups are methoxy, ethoxy, propoxy, butoxy, pentoxy, hexoxy and the like. Examples of branched alkoxy are isopropoxy, sec-butoxy, tert-butoxy, isopentyloxy, isohexyloxy and the like.

The term "$C_{3-6}$-cycloalkoxy" as used herein, alone or in combination, represent a saturated monocyclic hydrocarbon group having the indicated number of carbon atoms linked through an ether oxygen having its free valence bond from the ether oxygen. Examples of cycloalkoxy groups are cyclopropyloxy, cyclobutyloxy, cyclopentyloxy, cyclohexyloxy and the like.

The term "$C_{1-6}$-alkylthio" as used herein, alone or in combination, refers to a straight or branched monovalent substituent comprising a "$C_{1-6}$-alkyl" group as defined above linked through a divalent sulfur atom having its free valence bond from the sulfur atom and having 1 to 6 carbon atoms. Representative examples include, but are not limited to, methylthio, ethylthio, propylthio, butylthio, pentylthio and the like.

The term "$C_{3-6}$-cycloalkylthio" as used herein, alone or in combination, represent a saturated monocyclic hydrocarbon group having the indicated number of carbon atoms linked through a divalent sulfur atom having its free valence bond from the sulfur atom. Examples of cycloalkoxy groups are cyclopropylthio, cyclobutylthio, cyclopentylthio, cyclohexylthio and the like.

The term "$C_{1-6}$-alkylamino" as used herein, alone or in combination, refers to a straight or branched monovalent substituent comprising a "$C_{1-6}$-alkyl" group as defined above linked through amino having a free valence bond from the nitrogen atom. Representative examples include, but are not limited to, methylamino, ethylamino, propylamino, butylamino, pentylamino and the like.

The term "$C_{1-6}$-alkylaminocarbonyl" as used herein refers to a monovalent substituent comprising a $C_{1-6}$-monoalkylamino group linked through a carbonyl group such as e.g. methylaminocarbonyl, ethylaminocarbonyl, n-propylaminocarbonyl, isopropylaminocarbonyl, n-butyl-aminocarbonyl, sec-butylaminocarbonyl, isobutylaminocarbonyl, tert-butylaminocarbonyl, n-pentylaminocarbonyl, 2-methylbutylaminocarbonyl, 3-methylbutylaminocarbonyl, n-hexylaminocarbonyl, 4-methylpentylaminocarbonyl, neopentylaminocarbonyl, n-hexylaminocarbonyl and 2-2-dimethylpropylaminocarbonyl and the like.

The term "$C_{3-6}$-cycloalkylamino" as used herein, alone or in combination, represent a saturated monocyclic hydrocarbon group having the indicated number of carbon atoms linked through amino having a free valence bond from the nitrogen atom. Representative examples include, but are not limited to, cyclopropylamino, cyclobutylamino, cyclopentylamino, cyclohexylamino and the like.

The term "$C_{1-6}$-alkoxyC$_{1-6}$-alkyl" as used herein, alone or in combination, refers to a "$C_{1-6}$-alkyl" group as defined above whereto is attached a "$C_{1-6}$-alkoxy" group as defined above. Representative examples include, but are not limited to, methoxymethyl, ethoxymethyl, methoxyethyl, ethoxyethyl and the like.

The term "aryl" as used herein is intended to include monocyclic, bicyclic or polycyclic carbocyclic aromatic rings. Representative examples are phenyl, naphthyl (e.g. naphth-1-yl, naphth-2-yl), anthryl (e.g. anthr-1-yl, anthr-9-yl), phenanthryl (e.g. phenanthr-1-yl, phenanthr-9-yl), and the like. Aryl is also intended to include monocyclic, bicyclic or polycyclic carbocyclic aromatic rings substituted with carbocyclic aromatic rings. Representative examples are biphenyl (e.g. biphenyl-2-yl, biphenyl-3-yl, biphenyl-4-yl), phenylnaphthyl (e.g. 1-phenylnapth-2-yl, 2-phenylnaphth-1-yl), and the like. Aryl is also intended to include partially saturated bicyclic or polycyclic carbocyclic rings with at least one unsaturated moiety (e.g. a benzo moiety). Representative examples are, indanyl (e.g. indan-1-yl, indan-5-yl), indenyl (e.g. inden-1-yl, inden-5-yl), 1,2,3,4-tetrahydronaphthyl (e.g. 1,2,3,4-tetrahydronaphth-1-yl, 1,2,3,4-tetrahydronaphth-2-yl, 1,2,3,4-tetrahydronaphth-6-yl), 1,2-dihydronaphthyl (e.g. 1,2-dihydronaphth-1-yl, 1,2-dihydronaphth-4-yl, 1,2-dihydronaphth-6-yl), fluorenyl (e.g. fluoren-1-yl, fluoren-4-yl, fluoren-9-yl), and the like. Aryl is also intended to include partially saturated bicyclic or polycyclic carbocyclic aromatic rings containing one or two bridges. Representative examples are, benzonorbornyl (e.g. benzonorborn-3-yl, benzonorborn-6-yl), 1,4-ethano-1,2,3,4-tetrahydronapthyl (e.g. 1,4-ethano-1,2,3,4-tetrahydronapth-2-yl, 1,4-ethano-1,2,3,4-tetrahydronapth-10-yl), and the like. Aryl is also intended to include partially saturated bicyclic or polycyclic carbocyclic aromatic rings containing one or more spiro atoms. Representative examples are spiro[cyclopentane-1,1'-indane]-4-yl, spiro[cyclopentane-1,1'-indene]-4-yl, spiro[piperidine-4,1'-indane]-1-yl, spiro[piperidine-3,2'-indane]-1-yl, spiro[piperidine-4,2'-indane]-1-yl, spiro[piperidine-4,1'-indane]-3'-yl, spiro[pyrrolidine-3,2'-indane]-1-yl, spiro[pyrrolidine-3, 1'-(3',4'-dihydronaphthalene)]-1-yl, spiro[piperidine-3,1'-(3',4'-dihydronaphthalene)]-1-yl, spiro[piperidine-4,1'-(3',4'-dihydronaphthalene)]-1-yl, spiro[imidazolidine-4,2'-indane]-1-yl, spiro[piperidine-4,1'-indene]-1-yl, and the like. Other examples of "aryl" are phenyl, naphthyl, anthracenyl, phenanthrenyl, azulenyl, fluorenyl, indenyl and pentalenyl.

The term "arylene" as used herein refers to divalent aromatic monocyclic or a divalent aromatic fused bi- or tricyclic hydrocarbon group. Representative examples include, but are not limited to, phenylene, naphthylene and the like.

The term "arylcarbonyl" as used herein refers to the radical aryl-C(=O)—. Representative examples are benzoyl, naphthylcarbonyl, 4-phenylbenzoyl, anthrylcarbonyl, phenanthrylcarbonyl, azulenylcarbonyl and the like.

The term "heteroarylcarbonyl" as used herein refers to the radical heteroaryl-C(=O)—. Representative examples are pyridinylcarbonyl (e.g. pyridin-2-ylcarbonyl, pyridin-4-ylcarbonyl), quinolinylcarbonyl (e.g. 2-(quinolin-2-yl)carbonyl, 1-(quinolin-2-yl)carbonyl), imidazolylcarbonyl (e.g. imidazol-2-ylcarbonyl, imidazol-5-ylcarbonyl), and the like.

The term "arylsulfonyl" as used herein refers to an "aryl" group as defined above linked through a sulfonyl group. Representative examples include, but are not limited to, phenylsulfonyl, naphthylsulfonyl, anthracenylsulfonyl, phenanthrenylsulfonyl, azulenylsulfonyl, and the like.

The term "arylamido" as used herein refers to an arylcarbonyl group linked through an amino group. Representative examples include, but are not limited to phenylcarbonylamino, naphthylcarbonylamino, anthracenylcarbonylamino, phenanthrenylcarbonylamino, azulenylcarbonylamino and the like.

The term "halogen" means fluorine, chlorine, bromine or iodine.

The term "perhalomethyl" means trifluoromethyl, trichloromethyl, tribromomethyl or triiodomethyl.

The term "perhalomethoxy" means trifluoromethoxy, trichloromethoxy, tribromomethoxy or triiodomethoxy.

The term "$C_{1-6}$-dialkylamino" as used herein refers to an amino group wherein the two hydrogen atoms independently are substituted with a straight or branched, saturated hydrocarbon chain having the indicated number of carbon atoms. Representative examples include, but are not limited to, N,N-dimethylamino, N-ethyl-N-methylamino, N,N-diethylamino, N,N-dipropylamino (e.g. N,N-(prop-1-yl)$_2$-amino, N,N-(prop-2-yl)$_2$-amino, N,N-(prop-3-yl)$_2$-amino), N-(but-1-yl)-N-methylamino, N,N-(pent-1-yl)$_2$-amino, and the like.

The term "acyl" as used herein refers to a monovalent substituent comprising a "$C_{1-6}$-alkyl" group as defined above linked through a carbonyl group. Representative examples include, but are not limited to, acetyl, propionyl, butyryl, isobutyryl, pivaloyl, valeryl and the like.

The term "heteroaryl" as used herein, alone or in combination, refers to a monovalent substituent comprising a 5-7 membered monocyclic aromatic system or a 8-10 membered bicyclic aromatic system containing one or more heteroatoms selected from nitrogen, oxygen and sulphur. Examples of "heteroaryl" are pyrrolyl (e.g. pyrrol-1-yl, pyrrol-2-yl, pyrrol-3-yl), furanyl (e.g. furan-2-yl, furan-3-yl), thienyl (e.g. thien-2-yl, thien-3-yl), oxazolyl (e.g. oxazol-2-yl, oxazol-4-yl, oxazol-5-yl), thiazolyl (e.g. thiazol-2-yl, thiazol-4-yl, thiazol-5-yl), imidazolyl (e.g. imidazol-2-yl, imidazol-4-yl, imidazol-5-yl), pyrazolyl (e.g. pyrazol-1-yl, pyrazol-3-yl, pyrazol-5-yl), isoxazolyl (e.g. isoxazol-3-yl, isoxazol-4-yl, isoxazol-5-yl), isothiazolyl (e.g. isothiazol-3-yl, isothiazol-4-yl, isothiazol-5-yl), 1,2,3-triazolyl (e.g. 1,2,3-triazol-1-yl, 1,2,3-triazol-4-yl, 1,2,3-triazol-5-yl), 1,2,4-triazolyl (e.g. 1,2,4-triazol-1-yl, 1,2,4-triazol-3-yl, 1,2,4-triazol-5-yl), 1,2,3-oxadiazolyl (e.g. 1,2,3-oxadiazol-4-yl, 1,2,3-oxadiazol-5-yl), 1,2,4-oxadiazolyl (e.g. 1,2,4-oxadiazol-3-yl, 1,2,4-oxadiazol-5-yl), 1,2,5-oxadiazolyl (e.g. 1,2,5-oxadiazol-3-yl, 1,2,5-oxadiazol-4-yl), 1,3,4-oxadiazolyl (e.g. 1,3,4-oxadiazol-2-yl, 1,3,4-oxadiazol-5-yl), 1,2,3-thiadiazolyl (e.g. 1,2,3-thiadiazol-4-yl, 1,2,3-thiadiazol-5-yl), 1,2,4-thiadiazolyl (e.g. 1,2,4-thiadiazol-3-yl, 1,2,4-thiadiazol-5-yl), 1,2,5-thiadiazolyl (e.g. 1,2,5-thiadiazol-3-yl, 1,2,5-thiadiazol-4-yl), 1,3,4-thiadiazolyl (e.g. 1,3,4-thiadiazol-2-yl, 1,3,4-thiadiazol-5-yl), tetrazolyl (e.g. tetrazol-1-yl, tetrazol-5-yl), pyranyl (e.g. pyran-2-yl), pyridinyl (e.g. pyridine-2-yl, pyridine-3-yl, pyridine-4-yl), pyridazinyl (e.g. pyridazin-2-yl, pyridazin-3-yl), pyrimidinyl (e.g. pyrimidin-2-yl, pyrimidin-4-yl, pyrimidin-5-yl), pyrazinyl, 1,2,3-triazinyl, 1,2,4-triazinyl, 1,3,5-triazinyl, thiadiazinyl, azepinyl, azecinyl, indolyl (e.g. indol-1-yl, indol-2-yl, indol-3-yl, indol-5-yl), isoindolyl, benzofuranyl (e.g. benzo[b]furan-2-yl, benzo[b]furan-3-yl, benzo[b]furan-5-yl, benzo[c]furan-2-yl, benzo[c]furan-3-yl, benzo[c]furan-5-yl), benzothienyl (e.g. benzo[b]thien-2-yl, benzo[b]thien-3-yl, benzo[b]thien-5-yl, benzo[c]thien-2-yl, benzo-[c]thien-3-yl, benzo[c]thien-5-yl), indazolyl (e.g. indazol-1-yl, indazol-3-yl, indazol-5-yl), indolizinyl (e.g. indolizin-1-yl, indolizin-3-yl), benzopyranyl (e.g. benzo[b]pyran-3-yl, benzo-[b]pyran-6-yl, benzo[c]pyran-1-yl, benzo[c]pyran-7-yl), benzimidazolyl (e.g. benzimidazol-1-yl, benzimidazol-2-yl, benzimidazol-5-yl), benzothiazolyl (e.g. benzothiazol-2-yl, benzothiazol-5-yl), benzisothiazolyl, benzoxazolyl, benzisoxazolyl, benzoxazinyl, benzotriazolyl, naphthyridinyl (e.g. 1,8-naphthyridin-2-yl, 1,7-naphthyridin-2-yl, 1,6-naphthyridin-2-yl), phthalazinyl (e.g. phthalazin-1-yl, phthalazin-5-yl), pteridinyl, purinyl (e.g. purin-2-yl, purin-6-yl, purin-7-yl, purin-8-yl, purin-9-yl), quinazolinyl (e.g. quinazolin-2-yl, quinazolin-4-yl, quinazolin-6-yl), cinnolinyl, quinoliny (e.g. quinolin-2-yl, quinolin-3-yl, quinolin-4-yl, quinolin-6-yl), isoquinolinyl (e.g. isoquinolin-1-yl, isoquinolin-3-yl, isoquinolin-4-yl), quinoxalinyl (e.g. quinoxalin-2-yl, quinoxalin-5-yl), pyrrolopyridinyl (e.g. pyrrolo[2,3-b]pyridinyl, pyrrolo[2,3-c]pyridinyl, pyrrolo[3,2-c]pyridinyl), furopyridinyl (e.g. furo[2,3-b]pyridinyl, furo[2,3-c]pyridinyl, furo[3,2-c]pyridinyl), thienopyridinyl (e.g. thieno[2,3-b]pyridinyl, thieno[2,3-c]pyridinyl, thieno[3,2-c]pyridinyl), imidazopyridinyl (e.g. imidazo[4,5-b]pyridinyl, imidazo[4,5-c]pyridinyl, imidazo[1,5-a]pyridinyl, imidazo[1,2-a]pyridinyl), imidazopyrimidinyl (e.g. imidazo[1,2-a]pyrimidinyl, imidazo[3,4-a]pyrimidinyl), pyrazolopyridinyl (e.g. pyrazolo[3,4-b]pyridinyl, pyrazolo[3,4-c]pyridinyl, pyrazolo[1,5-a]pyridinyl), pyrazolopyrimidinyl (e.g. pyrazolo[1,5-a]pyrimidinyl, pyrazolo[3,4-d]pyrimidinyl), thiazolopyridinyl (e.g. thiazolo[3,2-d]pyridinyl), thiazolopyrimidinyl (e.g. thiazolo[5,4-d]pyrimidinyl), imdazothiazolyl (e.g. imidazo[2,1-b]thiazolyl), triazolopyridinyl (e.g. triazolo[4,5-b]pyridinyl), triazolopyrimidinyl (e.g. 8-azapurinyl), carbazolyl (e.g. carbazol-2-yl, carbazol-3-yl, carbazol-9-yl), phenoxazinyl (e.g. phenoxazin-10-yl), phenazinyl (e.g. phenazin-5-yl), acridinyl (e.g. acridin-9-yl, acridin-10-yl), phenothiazinyl (e.g. phenothiazin-10-yl), carbolinyl (e.g. pyrido[3,4-b]indol-1-yl, pyrido[3,4-b]indol-3-yl), phenanthrolinyl (e.g. phenanthrolin-5-yl), pyrrolinyl, pyrazolinyl, imidazolinyl (e.g. 4,5-dihydroimidazol-2-yl, 4,5-dihydroimidazol-1-yl), indolinyl (e.g. 2,3-dihydroindol-1-yl, 2,3-dihydroindol-5-yl), dihydrobenzofuranyl (e.g. 2,3-dihydrobenzo[b]furan-2-yl, 2,3-dihydrobenzo[b]furan-4-yl), dihydrobenzothienyl (e.g. 2,3-dihydrobenzo[b]thien-2-yl, 2,3-dihydrobenzo[b]thien-5-yl), 4,5,6,7-tetrahydrobenzo[b]furan-5-yl, dihydrobenzopyranyl (e.g. 3,4-dihydrobenzo[b]pyran-3-yl, 3,4-dihydrobenzo[b]pyran-6-yl, 3,4-dihydrobenzo[c]pyran-1-yl, dihydrobenzo[c]pyran-7-yl), oxazolinyl (e.g. 4,5-dihydrooxazol-2-yl, 4,5-dihydrooxazol-4-yl, 4,5-dihydrooxazol-5-yl), isoxazolinyl, oxazepinyl, tetrahydroindazolyl (e.g. 4,5,6,7-tetrahydroindazol-1-yl, 4,5,6,7-tetrahydroindazol-3-yl, 4,5,6,7-tetrahydroindazol-4-yl, 4,5,6,7-tetrahydroindazol-6-yl), tetrahydrobenzimidazolyl (e.g. 4,5,6,7-tetrahydrobenzimidazol-1-yl, 4,5,6,7-tetrahydrobenzimidazol-5-yl), tetrahydroimidazo[4,5-c]pyridyl (e.g. 4,5,6,7-tetrahydroimidazo-[4,5-c]pyrid-1-yl, 4,5,6,7-tetrahydroimidazo[4,5-c]pyrid-5-yl, 4,5,6,7-tetrahydroimidazo[4,5-c]pyrid-6-yl), tetrahydroquinolinyl (e.g. 1,2,3,4-tetrahydroquinolinyl, 5,6,7,8-tetrahydroquinolinyl), tetrahydroisoquinolinyl (e.g. 1,2,3,4-tetrahydroisoquinolinyl, 5,6,7,8-tetrahydroisoquinolinyl), tetrahydroquinoxalinyl (e.g. 1,2,3,4-tetrahydroquinoxalinyl, 5,6,7,8-tetrahydroquinoxalinyl), spiro[isoquinoline-3,1'-cyclohexan]-1-yl, spiro[piperidine-4,1'-benzo[c]thiophen]-1-yl, spiro[piperidine-4,1'-benzo[c]furan]-1-yl, spiro[piperidine-4,3'-benzo[b]furan]-1-yl, spiro-[piperidine-4,3'-coumarin]-1-yl. Other examples of "heteroaryl" are furyl, thienyl, pyrrolyl, imidazolyl, pyrazolyl, triazolyl, pyridyl, pyrazinyl, pyrimidinyl, pyridazinyl, isothiazolyl, isoxazolyl, oxazolyl, oxadiazolyl, thiadiazolyl, quinolyl, isoquinolyl, quinazolinyl, quinoxalinyl, indolyl, benzimidazolyl, benzofuranyl, benzothienyl, benzoxazolyl, tetrazolyl, carbazolyl, pteridinyl and purinyl.

The term "heteroarylene" as used herein, alone or in combination, refers to divalent 5-7 membered monocyclic aromatic system or a 8-10 membered bicyclic aromatic system containing one or more heteroatoms selected from nitrogen, oxygen and sulfur, e.g. furylene, thienylene, pyrrolylene, imidazolylene, pyrazolylene, triazolylene, pyridylene, pyrazinylene, pyrimidinylene, pyridazinylene, isothiazolylene, isoxazolylene, oxazolylene, oxadiazolylene, thiadiazolylene, quinolylene, isoquinolylene, quinazolinylene, quinoxalinylene, indolylene, benzimidazolylene, benzofuranylene, benzothienylene, pteridinylene and purinylene and the like.

The term "heteroaryloxy" as used herein, alone or in combination, refers to a heteroaryl as defined herein linked to an oxygen atom having its free valence bond from the oxygen atom e.g. pyrrolyloxy, imidazolyloxy, pyrazolyloxy, triazolyloxy, pyrazinyloxy, pyrimidinyloxy, pyridazinyloxy, isothiazolyloxy, isoxazolyloxy, oxazolyloxy, oxadiazolyloxy, thiadiazolyloxy, quinolinyloxy, isoquinolinyloxy, quinazolinyloxy, quinoxalinyloxy, indoltloxy, benzimidazolyloxy, benzofuranyloxy, pteridinyloxy and purinyloxy and the like.

The term "aralkyl" as used herein refers to a straight or branched saturated carbon chain containing from 1 to 6 carbons substituted with an aromatic carbohydride. Representative examples include, but are not limited to, benzyl, phenethyl, 3-phenylpropyl, 1-naphthylmethyl, 2-(1-naphthyl)ethyl and the like.

The term "aryloxy" as used herein refers to phenoxy, 1-naphthyloxy, 2-naphthyloxy and the like.

The term "aralkoxy" as used herein refers to a $C_{1-6}$-alkoxy group substituted with an aromatic carbohydride, such as benzyloxy, phenethoxy, 3-phenylpropoxy, 1-naphthylmethoxy, 2-(1-naphtyl)ethoxy and the like.

The term "heteroaralkyl" as used herein refers to a straight or branched saturated carbon chain containing from 1 to 6 carbons substituted with a heteroaryl group; such as (2-furyl)methyl, (3-furyl)methyl, (2-thienyl)methyl, (3-thienyl)methyl, (2-pyridyl)methyl, 1-methyl-1-(2-pyrimidyl)ethyl and the like.

The term "heteroaralkoxy" as used herein refers to a heteroarylalkyl as defined herein linked to an oxygen atom having its free valence bond from the oxygen atom. Representative examples include, but are not limited to, (2-furyl)methyl, (3-furyl)methyl, (2-thienyl)methyl, (3-thienyl)methyl, (2-pyridyl)methyl, 1-methyl-1-(2-pyrimidyl)ethyl linked to oxygen, and the like.

The term "arylthio" as used herein, alone or in combination, refers to an aryl group linked through a divalent sulfur atom having its free valence bond from the sulfur atom, the aryl group optionally being mono- or polysubstituted with $C_{1-6}$-alkyl, halogen, hydroxy or $C_{1-6}$-alkoxy. Representative examples include, but are not limited to, phenylthio, (4-methylphenyl)-thio, (2-chlorophenyl)thio and the like.

The term "Heterocyclyl" or "heterocycle" signifies a mono-, bi-, or tricyclic ring consisting of carbon atoms and from one heteroatom to the maximum number designated, wherein the heteroatom is selected from oxygen, nitrogen, and sulphur. If sulphur is present, then it can be S, S(O), or $S(O)_2$. If nitrogen is present, then it can be N, NH, substituted N, or N-oxide. The heterocycle is a saturated or partially saturated ring. From 0-2 $CH_2$ groups of the heterocycle can be replaced by C(O). The heterocycle can be attached via a carbon or nitrogen atom, unless linking the nitrogen atom would lead to a quaternary nitrogen. If the heterocycle is bicyclic, then one or both of the rings may have a heteroatom(s) present. If the heterocycle is tricyclic, then one, two, or all three of the rings may have a heteroatom(s) present. Examples of "heterocycle" are aziridinyl (e.g. aziridin-1-yl), azetidinyl (e.g. azetidin-1-yl, azetidin-3-yl), oxetanyl, pyrrolidinyl (e.g. pyrrolidin-1-yl, pyrrolidin-2-yl, pyrrolidin-3-yl), imidazolidinyl (e.g. imidazolidin-1-yl, imidazolidin-2-yl, imidazolidin-4-yl), oxazolidinyl (e.g. oxazolidin-2-yl, oxazolidin-3-yl, oxazolidin-4-yl), thiazolidinyl (e.g. thiazolidin-2-yl, thiazolidin-3-yl, thiazolidin-4-yl), isothiazolidinyl, piperidinyl (e.g. piperidin-1-yl, piperidin-2-yl, piperidin-3-yl, piperidin-4-yl), homopiperidinyl (e.g. homopiperidin-1-yl, homopiperidin-2-yl, homopiperidin-3-yl, homopiperidin-4-yl), piperazinyl (e.g. piperazin-1-yl, piperazin-2-yl), morpholinyl (e.g. morpholin-2-yl, morpholin-3-yl, morpholin-4-yl), thiomorpholinyl (e.g. thiomorpholin-2-yl, thiomorpholin-3-yl, thiomorpholin-4-yl), 1-oxo-thiomorpholinyl, 1,1-dioxo-thiomorpholinyl, tetrahydrofuranyl (e.g. tetrahydrofuran-2-yl, tetrahydrofuran-3-yl), tetrahydrothienyl, tetrahydro-1,1-dioxothienyl, tetrahydropyranyl (e.g. 2-tetrahydropyranyl), tetrahydrothiopyranyl (e.g. 2-tetrahydrothiopyranyl), 1,4-dioxanyl, 1,3-dioxanyl, octahydroindolyl (e.g. octahydroindol-1-yl, octahydroindol-2-yl, octahydroindol-3-yl, octahydroindol-5-yl), decahydroquinolinyl (e.g. decahydroquinolin-1-yl, decahydroquinolin-2-yl, decahydroquinolin-3-yl, decahydroquinolin-4-yl, decahydroquinolin-6-yl), decahydroquinoxalinyl (e.g. decahydroquinoxalin-1-yl, decahydroquinoxalin-2-yl, decahydroquinoxalin-6-yl), 3-azabicyclo[3.2.2]nonyl, 2-azabicyclo[2.2.1]heptyl, 3-azabicyclo[3.1.0]hexyl, 2,5-diazabicyclo-[2.2.1]heptyl, atropinyl, tropinyl, quinuclidinyl, 1,4-diazabicyclo[2.2.2]octanyl, 1,4-dioxaspiro-[4.5]decanyl (e.g. 1,4-dioxaspiro[4.5]decan-2-yl, 1,4-dioxaspiro[4.5]decan-7-yl), 1,4-dioxa-8-azaspiro[4.5]decanyl (e.g. 1,4-dioxa-8-azaspiro[4.5]decan-2-yl, 1,4-dioxa-8-azaspiro[4.5]-decan-8-yl), 8-azaspiro[4.5]decanyl (e.g. 8-azaspiro[4.5]decan-1-yl, 8-azaspiro[4.5]decan-8-yl), 2-azaspiro[5.5]undecanyl (e.g. 2-azaspiro[5.5]undecan-2-yl), 2,8-diazaspiro[4.5]decanyl (e.g. 2,8-diazaspiro[4.5]decan-2-yl, 2,8-diazaspiro[4.5]decan-8-yl), 2,8-diazaspiro[5.5]undecanyl (e.g. 2,8-diazaspiro[5.5]undecan-2-yl), 1,3,8-triazaspiro[4.5]decanyl (e.g. 1,3,8-triazaspiro-[4.5]decan-1-yl, 1,3,8-triazaspiro[4.5]decan-3-yl, and 1,3,8-triazaspiro[4.5]decan-8-yl). Other examples of "heterocycle" are pyrrolidinyl, pyrrolinyl, tetrahydrofuranyl, dihydrofuranyl, tetrahydrothiophenyl, dihydrothiophenyl, imidzolidinyl, imidazolinyl, pyrazolidinyl, pyrazolinyl, oxa-zolidinyl, oxazoline, isoxazolidinyl, isoxazoline, thioxazolidinyl, thioxazoline, isothioxazolidinyl, isothioxazoline, triazolidinyl, triazolinyl, tetrazolidinyl, tetrazolinyl, tetrahydropyranyl, dihydropyranyl, pyran, piperidinyl, piperazinyl, homopiperazinyl, morpholino, thiomorpholino, and 1,1-dioxothiomorpholino.

The term "heterocyclyl-$C_{1-6}$-alkyl" as used herein, alone or in combination, refers to a "$C_{1-6}$-alkyl" group as defined above whereto is attached a "heterocyclyl" group as defined above. Representative examples include, but are not limited to pyrrolidinylmethyl, imidazolinylmethyl, piperidinylmethyl, piperazinylmethyl, morpholinylmethyl, pyrrolidinylethyl, imidazolinylethyl, piperidinylethyl, piperazinylethyl, morpholinylethyl, pyrrolidinylpropyl, imidazolinylpropyl, piperidinylpropyl, piperazinylpropyl, morpholinylpropyl, and the like.

The term "aryl-$C_{2-6}$-alkynyl" as used herein, alone or in combination, refers to a "$C_{2-6}$-alkynyl" group as defined above whereto is attached a "aryl" group as defined above. Representative examples include, but are not limited to phenylpropynyl, naphthylpropynyl, indenylpropynyl, phenylbutynyl, naphthylbutynyl, indenylbutynyl, and the like.

The term "heterocyclyl-$C_{2-6}$-alkynyl" as used herein, alone or in combination, refers to a "$C_{2-6}$-alkynyl" group as defined above whereto is attached a "heterocyclyl" group as defined above. Representative examples include, but are not limited to pyrrolidinylpropynyl, imidazolinylpropynyl, piperidinylpropynyl, piperazinylpropynyl, morpholinylpropynyl, and the like.

The term "heteroaryl-$C_{2-6}$-alkynyl" as used herein, alone or in combination, refers to a "$C_{2-6}$-alkynyl" group as defined above whereto is attached a "heteroaryl" group as defined above. Representative examples include, but are not limited to furylpropynyl, thienylpropynyl, pyrrolylpropynyl, imidazolylpropynyl, pyrazolylpropynyl, quinolylpropynyl, benzofuranylpropynyl, and the like.

The term "aryl-$C_{2-6}$-alkenyl" as used herein, alone or in combination, refers to a "$C_{2-6}$-alkenyl" group as defined above whereto is attached a "aryl" group as defined above. Representative examples include, but are not limited to phenylvinyl, naphthylvinyl, indenylvinyl, phenylpropenyl, naphthylpropenyl, indenylpropenyl, and the like.

The term "heteroaryl-$C_{2-6}$-alkenyl" as used herein, alone or in combination, refers to a "$C_{2-6}$-alkenyl" group as defined above whereto is attached a "heteroaryl" group as defined above. Representative examples include, but are not limited to furylvinyl, thienylvinyl, pyrrolylvinyl, imidazolylvinyl, pyrazolylvinyl, quinolylvinyl, benzofuranylvinyl, furylpropenyl, thienylpropenyl, pyrrolylpropenyl, imidazolylpropenyl, pyrazolylpropenyl, quinolylpropenyl, benzofuranylpropenyl and the like.

The term "heterocyclyl-$C_{2-6}$-alkenyl" as used herein, alone or in combination, refers to a "$C_{2-6}$-alkenyl" group as defined above whereto is attached a "heterocyclyl" group as defined above. Representative examples include, but are not limited to pyrrolidinylvinyl, imidazolinylvinyl, piperidinylvinyl, piperazinylvinyl, morpholinylvinyl, pyrrolidinylpropenyl, imidazolinylpropenyl, piperidinylpropenyl, piperazinylpropenyl, morpholinylpropynyl, and the like.

The term "five to eight member ring" as used herein refers to a saturated or unsaturated, substituted or unsubstituted hydrocarbon chain or hydrocarbon-heteroatom chain having from 3 to 6 atoms wherein the carbon atom in Ar, to which they are attached, and the adjacent carbon atom form a five to eight member ring.

Certain of the above defined terms may occur more than once in the structural formulae, and upon such occurrence each term shall be defined independently of the other.

The term "optionally substituted" as used herein means that the groups in question are either unsubstituted or substituted with one or more of the substituents specified. When the groups in question are substituted with more than one substituent the substituents may be the same or different.

The term "prodrug" as used herein includes biohydrolyzable amides and biohydrolyzable esters and also encompasses a) compounds in which the biohydrolyzable functionality in such a prodrug is encompassed in the compound according to the present invention, and b) compounds which may be oxidized or reduced biologically at a given functional group to yield drug substances according to the present invention. Examples of these functional groups include 1,4-dihydropyridine, N-alkylcarbonyl-1,4-dihydropyridine, 1,4-cyclohexadiene, tert-butyl, and the like.

The term "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, e.g., arresting or slowing its development; and/or (c) relieving the disease-state, e.g., causing regression of the disease state itself or some symptom of the disease state.

The term "pharmaceutically acceptable" is defined as being suitable for administration to humans without adverse events.

The term "therapeutically effective amount" is intended to include an amount of a compound of the present invention that is effective when administered alone or in combination to activate glucokinase.

DESCRIPTION OF THE INVENTION

The present invention relates to compounds of the general formula (I):

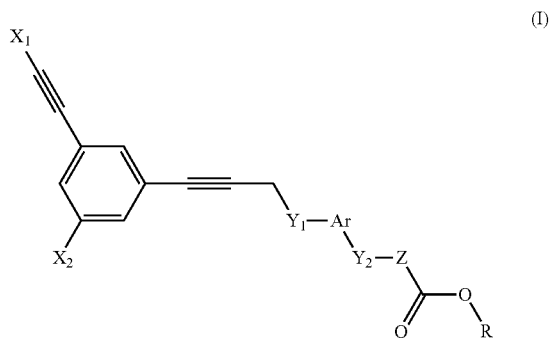

wherein $X_1$ is aryl, heteroaryl or heterocyclyl each of which is optionally substituted with one or more substituents selected from
  halogen, perhalomethyl, hydroxy, cyano, amino or carboxy; or
  $C_{1-6}$-alkyl, $C_{3-6}$-cycloalkyl, $C_{2-6}$-alkenyl, $C_{2-6}$-alkynyl, aryl, aralkyl, heteroaryl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkyl carbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted with one or more hydroxyl or halogens; or $X_1$ is aralkyl, heteroaralkyl or heterocyclyl-$C_{1-6}$-alkyl, each of which is optionally substituted with one or more substituents selected from halogen, perhalomethyl, hydroxy, cyano, amino or carboxy; or $C_{1-6}$-alkyl, $C_{3-6}$-cycloalkyl, $C_{2-6}$-alkenyl, $C_{2-6}$-alkynyl, aryl, aralkyl, heteroaryl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino each of which is optionally substituted with one or more hydroxyl or halogens;

$X_2$ is hydrogen or halogen; or $X_2$ is aryl-$C_{2-6}$-alkynyl, heteroaryl-$C_{2-6}$-alkynyl, heterocyclyl-$C_{2-6}$-alkynyl, aryl-$C_{2-6}$-alkenyl, heteroaryl-$C_{2-6}$-alkenyl, heterocyclyl-$C_{2-6}$-alkenyl, aryl or heteroaryl each of which is optionally substituted with one or more substituents selected from halogen, perhalomethyl, hydroxy, cyano, amino or carboxy; or $C_{1-6}$-alkyl, $C_{3-6}$-cycloalkyl, $C_{2-6}$-alkenyl, $C_{2-6}$-alkynyl, aryl, aralkyl, heteroaryl, heteroaralkyl, heterocyclyl-$C_{1-6}$- alkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino each of which is optionally substituted with one or more hydroxyl or halogens;

Ar is arylene which is optionally substituted with one or more substituents selected from halogen, hydroxy or cyano; or $C_{1-6}$-alkyl, $C_{3-6}$-cycloalkyl, $C_{2-6}$-alkenyl, $C_{2-6}$-alkynyl, aryl, heteroaryl, aralkyl, heteroaralkyl, $C_{1-6}$-alkoxy, $C_{3-6}$-cycloalkoxy, aryloxy, aralkoxy, heteroaralkoxy, $C_{1-6}$-alkylthio, arylthio or $C_{3-6}$-cycloalkylthio each of which is optionally substituted with one or more halogens; or two of the substituents when placed in adjacent positions together with the atoms to which they are attached may form a five to eight member ring; and $Y_1$ is O or S; and $Y_2$ is O or S; and Z is —$(CH_2)_n$— wherein n is 1, 2 or 3; and R is hydrogen, $C_{1-6}$-alkyl, $C_{3-6}$-cycloalkyl, $C_{2-6}$-alkenyl, $C_{2-6}$-alkynyl, $C_{4-6}$-alkenynyl or aryl; or a pharmaceutically acceptable salt thereof, or a pharmaceutically acceptable solvate thereof, or any tautomeric forms, stereoisomers, mixture of stereoisomers including a racemic mixture, or polymorphs.

In one embodiment, the present invention is concerned with compounds of formula (I) wherein $X_1$ is aryl, heteroaryl or heterocyclyl each of which is optionally substituted with one or more substituents selected from halogen, perhalomethyl, hydroxy or carboxy; or $C_{1-6}$-alkyl, $C_{3-6}$-cycloalkyl, aryl, aralkyl, heteroaryl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted with one or more halogens.

In another embodiment, the present invention is concerned with compounds of formula (I) wherein $X_1$ is aryl, heteroaryl or heterocyclyl each of which is optionally substituted with one or more substituents selected from halogen, perhalomethyl or hydroxy; or $C_{1-6}$-alkyl, $C_{3-6}$-cycloalkyl, aryl, aralkyl, heteroaryl, heteroaralkyl, $C_{1-6}$-alkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted with one or more halogens.

In another embodiment, the present invention is concerned with compounds of formula (I) wherein $X_1$ is aryl, heteroaryl or heterocyclyl each of which is optionally substituted with one or more substituents selected from halogen, perhalomethyl or hydroxy; or $C_{1-6}$-alkyl, $C_{3-6}$-cycloalkyl, aryl, aralkyl, $C_{1-6}$-alkoxy, $C_{1-6}$-alkylsulfonyl or arylsulfonyl, each of which is optionally substituted with one or more halogens.

In another embodiment, the present invention is concerned with compounds of formula (I) wherein $X_1$ is aryl, heteroaryl or heterocyclyl each of which is optionally substituted with one or more substituents selected from halogen, perhalomethyl or hydroxy; or $C_{1-6}$-alkyl, aryl, or $C_{1-6}$-alkylsulfonyl, each of which is optionally substituted with one or more halogens.

In another embodiment, the present invention is concerned with compounds of formula (I) wherein $X_1$ is aryl, which is optionally substituted with one or more substituents selected from halogen, perhalomethyl, hydroxy or carboxy; or $C_{1-6}$-alkyl, $C_{3-6}$-cycloalkyl, aryl, aralkyl, heteroaryl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted with one or more halogens.

In another embodiment, the present invention is concerned with compounds of formula (I) wherein $X_1$ is aryl, which is optionally substituted with one or more substituents selected from halogen, perhalomethyl or hydroxy; or $C_{1-6}$-alkyl, $C_{3-6}$-cycloalkyl, aryl, aralkyl, heteroaryl, heteroaralkyl, $C_{1-6}$-alkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted with one or more halogens.

In another embodiment, the present invention is concerned with compounds of formula (I) wherein $X_1$ is aryl, which is optionally substituted with one or more substituents selected from halogen, perhalomethyl or hydroxy; or $C_{1-6}$-alkyl, $C_{3-6}$-cycloalkyl, aryl, aralkyl, $C_{1-6}$-alkoxy, $C_{1-6}$-alkylsulfonyl or arylsulfonyl, each of which is optionally substituted with one or more halogens.

In another embodiment, the present invention is concerned with compounds of formula (I) wherein $X_1$ is aryl, which is optionally substituted with one or more substituents selected from
halogen, perhalomethyl or hydroxy; or
$C_{1-6}$-alkyl, aryl, or $C_{1-6}$-alkylsulfonyl, each of which is optionally substituted with one or more halogens.

In another embodiment, the present invention is concerned with compounds of formula (I) wherein $X_1$ is phenyl, which is optionally substituted with one or more substituents selected from
halogen, perhalomethyl, $C_{1-6}$-alkyl or $C_{1-6}$-alkylsulfonyl.

In another embodiment, the present invention is concerned with compounds of formula (I) wherein $X_1$ is heteroaryl, which is optionally substituted with one or more substituents selected from
halogen, perhalomethyl, hydroxy or carboxy; or
$C_{1-6}$-alkyl, $C_{3-6}$-cycloalkyl, aryl, aralkyl, heteroaryl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted with one or more halogens.

In another embodiment, the present invention is concerned with compounds of formula (I) wherein $X_1$ is heteroaryl, which is optionally substituted with one or more substituents selected from
halogen, perhalomethyl or hydroxy; or
$C_{1-6}$-alkyl, $C_{3-6}$-cycloalkyl, aryl, aralkyl, heteroaryl, heteroaralkyl, $C_{1-6}$-alkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted with one or more halogens.

In another embodiment, the present invention is concerned with compounds of formula (I) wherein $X_1$ is heteroaryl, which is optionally substituted with one or more substituents selected from
halogen, perhalomethyl or hydroxy; or
$C_{1-6}$-alkyl, $C_{3-6}$-cycloalkyl, aryl, aralkyl, $C_{1-6}$-alkoxy, $C_{1-6}$-alkylsulfonyl or arylsulfonyl, each of which is optionally substituted with one or more halogens.

In another embodiment, the present invention is concerned with compounds of formula (I) wherein $X_1$ is heteroaryl, which is optionally substituted with one or more substituents selected from
halogen, perhalomethyl or hydroxy; or
$C_{1-6}$-alkyl, aryl, or $C_{1-6}$-alkylsulfonyl, each of which is optionally substituted with one or more halogens.

In another embodiment, the present invention is concerned with compounds of formula (I) wherein $X_1$ is heterocyclyl, which is optionally substituted with one or more substituents selected from
halogen, perhalomethyl, hydroxy or carboxy; or
$C_{1-6}$-alkyl, $C_{3-6}$-cycloalkyl, aryl, aralkyl, heteroaryl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted with one or more halogens.

In another embodiment, the present invention is concerned with compounds of formula (I) wherein $X_1$ is heterocyclyl, which is optionally substituted with one or more substituents selected from
halogen, perhalomethyl or hydroxy; or
$C_{1-6}$-alkyl, $C_{3-6}$-cycloalkyl, aryl, aralkyl, heteroaryl, heteroaralkyl, $C_{1-6}$-alkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted with one or more halogens.

In another embodiment, the present invention is concerned with compounds of formula (I) wherein $X_1$ is heterocyclyl, which is optionally substituted with one or more substituents selected from
halogen, perhalomethyl or hydroxy; or
$C_{1-6}$-alkyl, $C_{3-6}$-cycloalkyl, aryl, aralkyl, $C_{1-6}$-alkoxy, $C_{1-6}$-alkylsulfonyl or arylsulfonyl, each of which is optionally substituted with one or more halogens.

In another embodiment, the present invention is concerned with compounds of formula (I) wherein $X_1$ is heterocyclyl, which is optionally substituted with one or more substituents selected from
halogen, perhalomethyl or hydroxy; or
$C_{1-6}$-alkyl, aryl, or $C_{1-6}$-alkylsulfonyl, each of which is optionally substituted with one or more halogens.

In another embodiment, the present invention is concerned with compounds of formula (I) wherein $X_1$ aralkyl, heteroaralkyl or heterocyclyl-$C_{1-6}$-alkyl each of which is optionally substituted with one or more substituents selected from
halogen, perhalomethyl, hydroxy or carboxy; or
$C_{1-6}$-alkyl, $C_{3-6}$-cycloalkyl, aryl, aralkyl, heteroaryl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted with one or more halogens.

In another embodiment, the present invention is concerned with compounds of formula (I) wherein $X_1$ is aralkyl, heteroaralkyl or heterocyclyl-$C_{1-6}$-alkyl each of which is optionally substituted with one or more substituents selected from
halogen, perhalomethyl or hydroxy; or
$C_{1-6}$-alkyl, $C_{3-6}$-cycloalkyl, aryl, aralkyl, heteroaryl, heteroaralkyl, $C_{1-6}$-alkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted with one or more halogens.

In another embodiment, the present invention is concerned with compounds of formula (I) wherein $X_1$ is aralkyl, heteroaralkyl or heterocyclyl-$C_{1-6}$-alkyl each of which is optionally substituted with one or more substituents selected from
halogen, perhalomethyl or hydroxy; or
$C_{1-6}$-alkyl, $C_{3-6}$-cycloalkyl, aryl, aralkyl, $C_{1-6}$-alkoxy, $C_{1-6}$-alkylsulfonyl or arylsulfonyl, each of which is optionally substituted with one or more halogens.

In another embodiment, the present invention is concerned with compounds of formula (I) wherein $X_1$ is aralkyl, heteroaralkyl or heterocyclyl-$C_{1-6}$-alkyl, each of which is optionally substituted with one or more substituents selected from halogen, perhalomethyl or hydroxy; or $C_{1-6}$-alkyl, aryl, or $C_{1-6}$-alkylsulfonyl, each of which is optionally substituted with one or more halogens.

In another embodiment, the present invention is concerned with compounds of formula (I) wherein $X_1$ is aralkyl, which is optionally substituted with one or more substituents selected from halogen, perhalomethyl, hydroxy or carboxy; or $C_{1-6}$-alkyl, $C_{3-6}$-cycloalkyl, aryl, aralkyl, heteroaryl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted with one or more halogens.

In another embodiment, the present invention is concerned with compounds of formula (I) wherein $X_1$ is aralkyl, which is optionally substituted with one or more substituents selected from halogen, perhalomethyl or hydroxy; or $C_{1-6}$-alkyl, $C_{3-6}$-cycloalkyl, aryl, aralkyl, heteroaryl, heteroaralkyl, $C_{1-6}$-alkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted with one or more halogens.

In another embodiment, the present invention is concerned with compounds of formula (I) wherein $X_1$ is aralkyl, which is optionally substituted with one or more substituents selected from halogen, perhalomethyl or hydroxy; or $C_{1-6}$-alkyl, $C_{3-6}$-cycloalkyl, aryl, aralkyl, $C_{1-6}$-alkoxy, $C_{1-6}$-alkylsulfonyl or arylsulfonyl, each of which is optionally substituted with one or more halogens.

In another embodiment, the present invention is concerned with compounds of formula (I) wherein $X_1$ is aralkyl, which is optionally substituted with one or more substituents selected from halogen, perhalomethyl or hydroxy; or $C_{1-6}$-alkyl, aryl, or $C_{1-6}$-alkylsulfonyl, each of which is optionally substituted with one or more halogens.

In another embodiment, the present invention is concerned with compounds of formula (I) wherein $X_1$ is heteroaralkyl, which is optionally substituted with one or more substituents selected from halogen, perhalomethyl, hydroxy or carboxy; or $C_{1-6}$-alkyl, $C_{3-6}$-cycloalkyl, aryl, aralkyl, heteroaryl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted with one or more halogens.

In another embodiment, the present invention is concerned with compounds of formula (I) wherein $X_1$ is heteroaralkyl, which is optionally substituted with one or more substituents selected from halogen, perhalomethyl or hydroxy; or $C_{1-6}$-alkyl, $C_{3-6}$-cycloalkyl, aryl, aralkyl, $C_{1-6}$-alkoxy, $C_{1-6}$-alkylsulfonyl or arylsulfonyl, each of which is optionally substituted with one or more halogens.

In another embodiment, the present invention is concerned with compounds of formula (I) wherein $X_1$ is heteroaralkyl, which is optionally substituted with one or more substituents selected from halogen, perhalomethyl or hydroxy; or $C_{1-6}$-alkyl, aryl, or $C_{1-6}$-alkylsulfonyl, each of which is optionally substituted with one or more halogens.

In another embodiment, the present invention is concerned with compounds of formula (I) wherein $X_1$ is heterocyclyl-$C_{1-6}$-alkyl, which is optionally substituted with one or more substituents selected from halogen, perhalomethyl, hydroxy or carboxy; or $C_{1-6}$-alkyl, $C_{3-6}$-cycloalkyl, aryl, aralkyl, heteroaryl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted with one or more halogens.

In another embodiment, the present invention is concerned with compounds of formula (I) wherein $X_1$ is heterocyclyl-$C_{1-6}$-alkyl, which is optionally substituted with one or more substituents selected from halogen, perhalomethyl or hydroxy; or $C_{1-6}$-alkyl, $C_{3-6}$-cycloalkyl, aryl, aralkyl, heteroaryl, heteroaralkyl, $C_{1-6}$-alkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted with one or more halogens.

In another embodiment, the present invention is concerned with compounds of formula (I) wherein $X_1$ is heterocyclyl-$C_{1-6}$-alkyl, which is optionally substituted with one or more substituents selected from halogen, perhalomethyl or hydroxy; or $C_{1-6}$-alkyl, $C_{3-6}$-cycloalkyl, aryl, aralkyl, $C_{1-6}$-alkoxy, $C_{1-6}$-alkylsulfonyl or arylsulfonyl, each of which is optionally substituted with one or more halogens.

In another embodiment, the present invention is concerned with compounds of formula (I) wherein $X_1$ is heterocyclyl-$C_{1-6}$-alkyl, which is optionally substituted with one or more substituents selected from halogen, perhalomethyl or hydroxy; or $C_{1-6}$-alkyl, aryl, or $C_{1-6}$-alkylsulfonyl, each of which is optionally substituted with one or more halogens.

In another embodiment, the present invention is concerned with compounds of formula (I) wherein $X_1$ is piperidinylmethylene or morpholinylmethylene.

In another embodiment the present invention is concerned with compounds of formula (I) wherein $X_2$ is hydrogen.

In another embodiment the present invention is concerned with compounds of formula (I) wherein $X_2$ is halogen.

In another embodiment the present invention is concerned with compounds of formula (I) wherein $X_2$ is bromine.

In another embodiment the present invention is concerned with compounds of formula (I) wherein $X_2$ is aryl-$C_{2-6}$-alkynyl, heteroaryl-$C_{2-6}$-alkynyl, heterocyclyl-$C_{2-6}$-alkynyl, aryl$C_{2-6}$-alkenyl, heteroaryl-$C_{2-6}$-alkenyl, heterocyclyl-$C_{2-6}$-alkenyl, aryl or heteroaryl each of which is optionally substituted with one or more substituents selected from halogen, perhalomethyl, hydroxy or carboxy; or $C_{1-6}$-alkyl, $C_{3-6}$-cycloalkyl, aryl, aralkyl, heteroaryl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted with one or more halogens.

In another embodiment the present invention is concerned with compounds of formula (I) wherein $X_2$ is aryl-$C_{2-6}$-alkynyl, heteroaryl-$C_{2-6}$-alkynyl, heterocyclyl-$C_{2-6}$-alkynyl, aryl$C_{2-6}$-alkenyl, heteroaryl-$C_{2-6}$-alkenyl, heterocyclyl-$C_{2-6}$-alkenyl, aryl or heteroaryl each of which is optionally substituted with one or more substituents selected from halogen, perhalomethyl or hydroxy; or $C_{1-6}$-alkyl, $C_{3-6}$-cycloalkyl, aryl, aralkyl, heteroaryl, heteroaralkyl, $C_{1-6}$-alkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted with one or more halogens.

In another embodiment, the present invention is concerned with compounds of formula (I) wherein $X_2$ is aryl-$C_{2-6}$-alkynyl, heteroaryl-$C_{2-6}$-alkynyl, heterocyclyl-$C_{2-6}$-alkynyl, aryl$C_{2-6}$-alkenyl, heteroaryl-$C_{2-6}$-alkenyl, heterocyclyl-$C_{2-6}$-alkenyl, aryl or heteroaryl each of which is optionally substituted with one or more substituents selected from halogen, perhalomethyl or hydroxy; or $C_{1-6}$-alkyl, $C_{3-6}$-cycloalkyl, aryl, aralkyl, $C_{1-6}$-alkoxy, $C_{1-6}$-alkylsulfonyl or arylsulfonyl, each of which is optionally substituted with one or more halogens.

In another embodiment, the present invention is concerned with compounds of formula (I) wherein $X_2$ aryl-$C_{2-6}$-alkynyl, heteroaryl-$C_{2-6}$-alkynyl, heterocyclyl-$C_{2-6}$-alkynyl, aryl-$C_{2-6}$-alkenyl, heteroaryl-$C_{2-6}$-alkenyl, heterocyclyl-$C_{2-6}$-alkenyl, aryl or heteroaryl each of which is optionally substituted with one or more substituents selected from halogen, perhalomethyl or hydroxy; or $C_{1-6}$-alkyl, aryl, or $C_{1-6}$-alkylsulfonyl, each of which is optionally substituted with one or more halogens.

In another embodiment the present invention is concerned with compounds of formula (I) wherein $X_2$ is aryl-$C_{2-6}$-alkynyl, which is optionally substituted with one or more substituents selected from halogen, perhalomethyl, hydroxy or carboxy; or $C_{1-6}$-alkyl, $C_{3-6}$-cycloalkyl, aryl, aralkyl, heteroaryl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted with one or more halogens.

In another embodiment the present invention is concerned with compounds of formula (I) wherein $X_2$ is aryl-$C_{2-6}$-alkynyl, which is optionally substituted with one or more substituents selected from halogen, perhalomethyl or hydroxy; or $C_{1-6}$-alkyl, $C_{3-6}$-cycloalkyl, aryl, aralkyl, heteroaryl, heteroaralkyl, $C_{1-6}$-alkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted with one or more halogens.

In another embodiment, the present invention is concerned with compounds of formula (I) wherein $X_2$ is aryl-$C_{2-6}$-alkynyl, which is optionally substituted with one or more substituents selected from halogen, perhalomethyl or hydroxy; or $C_{1-6}$-alkyl, $C_{3-6}$-cycloalkyl, aryl, aralkyl, $C_{1-6}$-alkoxy, $C_{1-6}$-alkylsulfonyl or arylsulfonyl, each of which is optionally substituted with one or more halogens.

In another embodiment, the present invention is concerned with compounds of formula (I) wherein $X_2$ is aryl-$C_{2-6}$-alkynyl, which is optionally substituted with one or more substituents selected from halogen, perhalomethyl or hydroxy; or $C_{1-6}$-alkyl, aryl, or $C_{1-6}$-alkylsulfonyl, each of which is optionally substituted with one or more halogens.

In another embodiment, the present invention is concerned with compounds of formula (I) wherein $X_2$ is phenylethynyl, which is optionally substituted with one or more substituents selected from halogen, perhalomethyl or hydroxy; or $C_{1-6}$-alkyl, aryl, or $C_{1-6}$-alkylsulfonyl.

In another embodiment the present invention is concerned with compounds of formula (I) wherein $X_2$ is heteroaryl-$C_{2-6}$-alkynyl, which is optionally substituted with one or more substituents selected from halogen, perhalomethyl, hydroxy or carboxy; or $C_{1-6}$-alkyl, $C_{3-6}$-cycloalkyl, aryl, aralkyl, heteroaryl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted with one or more halogens.

In another embodiment the present invention is concerned with compounds of formula (I) wherein $X_2$ is heteroaryl-$C_{2-6}$-alkynyl, which is optionally substituted with one or more substituents selected from halogen, perhalomethyl or hydroxy; or $C_{1-6}$-alkyl, $C_{3-6}$-cycloalkyl, aryl, aralkyl, heteroaryl, heteroaralkyl, $C_{1-6}$-alkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted with one or more halogens.

In another embodiment, the present invention is concerned with compounds of formula (I) wherein $X_2$ is heteroaryl-$C_{2-6}$-alkynyl, which is optionally substituted with one or more substituents selected from
- halogen, perhalomethyl or hydroxy; or
- $C_{1-6}$-alkyl, $C_{3-6}$-cycloalkyl, aryl, aralkyl, $C_{1-6}$-alkoxy, $C_{1-6}$-alkylsulfonyl or arylsulfonyl, each of which is optionally substituted with one or more halogens.

In another embodiment, the present invention is concerned with compounds of formula (I) wherein $X_2$ is heteroaryl-$C_{2-6}$-alkynyl, which is optionally substituted with one or more substituents selected from
- halogen, perhalomethyl or hydroxy; or
- $C_{1-6}$-alkyl, aryl, or $C_{1-6}$-alkylsulfonyl, each of which is optionally substituted with one or more halogens.

In another embodiment the present invention is concerned with compounds of formula (I) wherein $X_2$ is heterocyclyl-$C_{2-6}$-alkynyl, which is optionally substituted with one or more substituents selected from
- halogen, perhalomethyl, hydroxy or carboxy; or
- $C_{1-6}$-alkyl, $C_{3-6}$-cycloalkyl, aryl, aralkyl, heteroaryl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted with one or more halogens.

In another embodiment the present invention is concerned with compounds of formula (I) wherein $X_2$ is heterocyclyl-$C_{2-6}$-alkynyl, which is optionally substituted with one or more substituents selected from
- halogen, perhalomethyl or hydroxy; or
- $C_{1-6}$-alkyl, $C_{3-6}$-cycloalkyl, aryl, aralkyl, heteroaryl, heteroaralkyl, $C_{1-6}$-alkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted with one or more halogens.

In another embodiment, the present invention is concerned with compounds of formula (I) wherein $X_2$ is heterocyclyl-$C_{2-6}$-alkynyl, which is optionally substituted with one or more substituents selected from
- halogen, perhalomethyl or hydroxy; or
- $C_{1-6}$-alkyl, $C_{3-6}$-cycloalkyl, aryl, aralkyl, $C_{1-6}$-alkoxy, $C_{1-6}$-alkylsulfonyl or arylsulfonyl, each of which is optionally substituted with one or more halogens.

In another embodiment, the present invention is concerned with compounds of formula (I) wherein $X_2$ is heterocyclyl-$C_{2-6}$-alkynyl, which is optionally substituted with one or more substituents selected from
- halogen, perhalomethyl or hydroxy; or
- $C_{1-6}$-alkyl, aryl, or $C_{1-6}$-alkylsulfonyl, each of which is optionally substituted with one or more halogens.

In another embodiment, the present invention is concerned with compounds of formula (I) wherein $X_2$ is piperidinylpropynyl or morpholinylpropenyl, which is optionally substituted with one or more substituents selected from
- halogen, perhalomethyl or hydroxy; or
- $C_{1-6}$-alkyl, aryl, or $C_{1-6}$-alkylsulfonyl, each of which is optionally substituted with one or more halogens.

In another embodiment, the present invention is concerned with compounds of formula (I) wherein $X_2$ is aryl-$C_{2-6}$-alkenyl, heteroaryl-$C_{2-6}$-alkenyl or heterocyclyl-$C_{2-6}$-alkenyl, each of which is optionally substituted with one or more substituents selected from
- halogen, perhalomethyl, hydroxy or carboxy; or
- $C_{1-6}$-alkyl, $C_{3-6}$-cycloalkyl, aryl, aralkyl, heteroaryl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted with one or more halogens.

In another embodiment the present invention is concerned with compounds of formula (I) wherein $X_2$ is aryl-$C_{2-6}$-alkenyl, heteroaryl-$C_{2-6}$-alkenyl or heterocyclyl-$C_{2-6}$-alkenyl, each of which is optionally substituted with one or more substituents selected from
- halogen, perhalomethyl or hydroxy; or
- $C_{1-6}$-alkyl, $C_{3-6}$-cycloalkyl, aryl, aralkyl, heteroaryl, heteroaralkyl, $C_{1-6}$-alkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted with one or more halogens.

In another embodiment, the present invention is concerned with compounds of formula (I) wherein $X_2$ is aryl-$C_{2-6}$-alkenyl, heteroaryl-$C_{2-6}$-alkenyl or heterocyclyl-$C_{2-6}$-alkenyl, each of which is optionally substituted with one or more substituents selected from
- halogen, perhalomethyl or hydroxy; or
- $C_{1-6}$-alkyl, $C_{3-6}$-cycloalkyl, aryl, aralkyl, $C_{1-6}$-alkoxy, $C_{1-6}$-alkylsulfonyl or arylsulfonyl, each of which is optionally substituted with one or more halogens.

In another embodiment, the present invention is concerned with compounds of formula (I) wherein $X_2$ is aryl-$C_{2-6}$-alkenyl, heteroaryl-$C_{2-6}$-alkenyl or heterocyclyl-$C_{2-6}$-alkenyl, each of which is optionally substituted with one or more substituents selected from
- halogen, perhalomethyl or hydroxy; or
- $C_{1-6}$-alkyl, aryl, or $C_{1-6}$-alkylsulfonyl, each of which is optionally substituted with one or more halogens.

In another embodiment the present invention is concerned with compounds of formula (I) wherein $X_2$ is aryl, which is optionally substituted with one or more substituents selected from
- halogen, perhalomethyl, hydroxy or carboxy; or
- $C_{1-6}$-alkyl, $C_{3-6}$-cycloalkyl, aryl, aralkyl, heteroaryl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted with one or more halogens.

In another embodiment the present invention is concerned with compounds of formula (I) wherein $X_2$ is aryl, which is optionally substituted with one or more substituents selected from
- halogen, perhalomethyl or hydroxy; or
- $C_{1-6}$-alkyl, $C_{3-6}$-cycloalkyl, aryl, aralkyl, heteroaryl, heteroaralkyl, $C_{1-6}$-alkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted with one or more halogens.

In another embodiment, the present invention is concerned with compounds of formula (I) wherein $X_2$ is aryl, which is optionally substituted with one or more substituents selected from halogen, perhalomethyl or hydroxy; or $C_{1-6}$-alkyl, $C_{3-6}$-cycloalkyl, aryl, aralkyl, $C_{1-6}$-alkoxy, $C_{1-6}$-alkylsulfonyl or arylsulfonyl, each of which is optionally substituted with one or more halogens.

In another embodiment, the present invention is concerned with compounds of formula (I) wherein $X_2$ is aryl, which is optionally substituted with one or more substituents selected from halogen, perhalomethyl or hydroxy; or $C_{1-6}$-alkyl, aryl, or $C_{1-6}$-alkylsulfonyl, each of which is optionally substituted with one or more halogens.

In another embodiment the present invention is concerned with compounds of formula (I) wherein $X_2$ is heteroaryl, which is optionally substituted with one or more substituents selected from halogen, perhalomethyl, hydroxy or carboxy; or $C_{1-6}$-alkyl, $C_{3-6}$-cycloalkyl, aryl, aralkyl, heteroaryl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted with one or more halogens.

In another embodiment the present invention is concerned with compounds of formula (I) wherein $X_2$ is heteroaryl, which is optionally substituted with one or more substituents selected from halogen, perhalomethyl or hydroxy; or $C_{1-6}$-alkyl, $C_{3-6}$-cycloalkyl, aryl, aralkyl, heteroaryl, heteroaralkyl, $C_{1-6}$-alkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted with one or more halogens.

In another embodiment, the present invention is concerned with compounds of formula (I) wherein $X_2$ is heteroaryl, which is optionally substituted with one or more substituents selected from halogen, perhalomethyl or hydroxy; or $C_{1-6}$-alkyl, $C_{3-6}$-cycloalkyl, aryl, aralkyl, $C_{1-6}$-alkoxy, $C_{1-6}$-alkylsulfonyl or arylsulfonyl, each of which is optionally substituted with one or more halogens.

In another embodiment, the present invention is concerned with compounds of formula (I) wherein $X_2$ is heteroaryl, which is optionally substituted with one or more substituents selected from halogen, perhalomethyl or hydroxy; or $C_{1-6}$-alkyl, aryl, or $C_{1-6}$-alkylsulfonyl, each of which is optionally substituted with one or more halogens.

In another embodiment, the present invention is concerned with compounds of formula (I) wherein Ar is arylene which is optionally substituted with one or more substituents selected from halogen; or $C_{1-6}$-alkyl, $C_{1-6}$-alkoxy, aryloxy or aralkoxy each of which is optionally substituted with one or more halogens; or two of the substituents when placed in adjacent positions together with the atoms to which they are attached form a five membered carbon cycle.

In another embodiment, the present invention is concerned with compounds of formula (I) wherein Ar is phenylene which is optionally substituted with one or more substituents selected from halogen; or $C_{1-6}$-alkyl, $C_{1-6}$-alkoxy, aryloxy or aralkoxy each of which is optionally substituted with one or more halogens; or two of the substituents when placed in adjacent positions together with the atoms to which they are attached form a five membered carbon cycle.

In another embodiment, the present invention is concerned with compounds of formula (I) wherein Ar is phenylene which is optionally substituted with one or more substituents selected from halogen or $C_{1-6}$-alkyl.

In another embodiment, the present invention is concerned with compounds of formula (I) wherein Ar is phenylene which is optionally substituted with halogen.

In another embodiment, the present invention is concerned with compounds of formula (I) wherein Ar is phenylene which is optionally substituted with one or more of $C_{1-6}$-alkyl optionally substituted with one or more halogens.

In another embodiment, the present invention is concerned with compounds of formula (I) wherein Ar is phenylene which is optionally substituted with one or more of $C_{1-6}$-alkoxy optionally substituted with one or more halogens.

In another embodiment, the present invention is concerned with compounds of formula (I) wherein Ar is phenylene which is optionally substituted with one or more of aryloxy optionally substituted with one or more halogens.

In another embodiment, the present invention is concerned with compounds of formula (I) wherein Ar is phenylene which is optionally substituted with one or more of aralkoxy optionally substituted with one or more halogens.

In another embodiment, the present invention is concerned with compounds of formula (I) wherein Ar is phenylene which is optionally substituted with methyl.

In another embodiment, the present invention is concerned with compounds of formula (I) wherein Ar is phenylene.

In another embodiment, the present invention is concerned with compounds of formula (I) wherein $Y_1$ is S.

In another embodiment, the present invention is concerned with compounds of formula (I) wherein $Y_1$ is O.

In another embodiment, the present invention is concerned with compounds of formula (I) wherein $Y_2$ is O.

In another embodiment, the present invention is concerned with compounds of formula (I) wherein $Y_2$ is S.

In another embodiment, the present invention is concerned with compounds of formula (I) wherein $Y_2$ is $CH_2$.

In another embodiment, the present invention is concerned with compounds of formula (I) wherein n is 1.

In another embodiment, the present invention is concerned with compounds of formula (I) wherein n is 2.

In another embodiment, the present invention is concerned with compounds of formula (I) wherein R is hydrogen or $C_{1-6}$-alkyl.

In another embodiment, the present invention is concerned with compounds of formula (I) wherein R is hydrogen.

In another embodiment, the present invention is concerned with compounds of formula (I) wherein R is methyl or ethyl.

In another embodiment, the present invention is concerned with compounds of formula I wherein alkyl is methyl or ethyl.

In another embodiment, the present invention is concerned with compounds of formula I wherein alkenyl is vinyl or 1-propenyl.

In another embodiment, the present invention is concerned with compounds of formula I wherein alkynyl is 1-propynyl.

In another embodiment, the present invention is concerned with compounds of formula I wherein alkenynyl is 1-pentene-4-yne.

In another embodiment, the present invention is concerned with compounds of formula I wherein alkoxy is methoxy, ethoxy, isopropoxy or cyclopropoxy.

In another embodiment, the present invention is concerned with compounds of formula I wherein aryl is phenyl.

In another embodiment, the present invention is concerned with compounds of formula I wherein arylene is phenylene.

In another embodiment, the present invention is concerned with compounds of formula I wherein halogen is bromine, fluorine or chlorine.

In another embodiment, the present invention is concerned with compounds of formula I wherein perhalomethyl is trifluoromethyl.

In another embodiment, the present invention is concerned with compounds of formula I wherein perhalomethoxy is trifluoromethoxy, In another embodiment, the present invention is concerned with compounds of formula I wherein heteroaryl is furyl or thienyl.

In another embodiment, the present invention is concerned with compounds of formula I wherein heteroaryl is pyrazolyl, pyrrolyl or pyridyl.

In another embodiment, the present invention is concerned with compounds of formula I wherein heteroaryl is benzofuryl or benzothienyl.

In another embodiment, the present invention is concerned with compounds of formula I wherein heterocyclyl is pyrrolidinyl, piperidinyl, piperazinyl or morpholinyl.

In another embodiment, the present invention is concerned with compounds of formula I wherein heteroarylene is thienylene.

In another embodiment, the present invention is concerned with compounds of formula I wherein aralkyl is benzyl.

In another embodiment, the present invention is concerned with compounds of formula I wherein aryloxy is phenoxy.

In another embodiment, the present invention is concerned with compounds of formula I wherein aralkoxy is benzyloxy.

In another embodiment, the present invention is concerned with compounds of formula I which are PPARδ agonists.

In another embodiment, the present invention is concerned with compounds of formula I which are selective PPARδ agonists.

In another embodiment, the present invention is concerned with compounds of formula I which are selective, partial PPARδ agonists.

Examples of compounds of the invention are:
{4-[3-(3-Bromo-5-phenylethynyl-phenyl)-prop-2-ynyloxy]-phenoxy}-acetic acid;
{4-[3-(3,5-Bis-phenylethynyl-phenyl)-prop-2-ynyloxy]-phenoxy}-acetic acid;
(4-{3-[3-Bromo-5-(3-piperidin-1-yl-prop-1-ynyl)-phenyl]-prop-2-ynyloxy}-2-methyl-phenoxy)-acetic acid;
(2-Methyl-4-{3-[3-(3-piperidin-1-yl-prop-1-ynyl)-5-(4-trifluoromethyl-phenylethynyl)-phenyl]-prop-2-ynyloxy}-phenoxy)-acetic acid;
(4-{3-[3,5-Bis-(3-piperidin-1-yl-prop-1-ynyl)-phenyl]-prop-2-ynyloxy}-2-methyl-phenoxy)-acetic acid;
(4-{3-[3-Bromo-5-(3-morpholin-4-yl-prop-1-ynyl)-phenyl]-prop-2-ynyloxy}-2-methyl-phenoxy)-acetic acid;
(2-Methyl-4-{3-[3-(3-morpholin-4-yl-prop-1-ynyl)-5-(4-trifluoromethyl-phenylethynyl)-phenyl]-prop-2-ynyloxy}-phenoxy)-acetic acid;
(2-Methyl-4-{3-[3-(3-morpholin-4-yl-prop-1-ynyl)-5-phenylethynyl-phenyl]-prop-2-ynyloxy}-phenoxy)-acetic acid;
(4-{3-[3-(4-Chloro-phenylethynyl)-5-(3-morpholin-4-yl-prop-1-ynyl)-phenyl]-prop-2-ynyloxy}-2-methyl-phenoxy)-acetic acid;
(4-{3-[3-(4-Methanesulfonyl-phenylethynyl)-5-(3-morpholin-4-yl-prop-1-ynyl)-phenyl]-prop-2-ynyloxy}-2-methyl-phenoxy)-acetic acid;
(4-{3-[3-Bromo-5-(4-trifluoromethyl-phenylethynyl)-phenyl]-prop-2-ynyloxy}-2-methyl-phenoxy)-acetic acid; or
a salt thereof with a pharmaceutically acceptable acid or base, or any optical isomer or mixture of optical isomers, including a racemic mixture, or any tautomeric forms.

The present invention also encompasses pharmaceutically acceptable salts of the present compounds. Such salts include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium, zinc, calcium salts and the like. Examples of amines and organic amines include ammonium, methylamine, dimethylamine, trimethylamine, ethylamine, diethylamine, propylamine, butylamine, tetramethylamine, ethanolamine, diethanolamine, triethanolamine, meglumine, ethylenediamine, choline, N N'-dibenzylethylenediamine, N-benzylphenylethylamine, N-methyl-D-glucamine, guanidine and the like. Examples of cationic amino acids include lysine, arginine, histidine and the like.

The pharmaceutically acceptable salts are prepared by reacting the compound of formula I with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol etc. Mixture of solvents may be used. Organic bases like lysine, arginine, diethanolamine, choline, guandine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane etc. Mixture of solvents may also be used.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, enzymatic resolution, resolving the diastereomeric salts formed with chiral acids such as mandelic acid, camphorsulfonic acid, tartaric acid, lactic acid, and the like wherever applicable or chiral bases such as brucine, (R)- or (S)-phenylethylamine, cinchona alkaloids and their derivatives and the like. Commonly used methods are compiled by Jaques et al in "Enantiomers, Racemates and Resolution" (Wiley Interscience, 1981). More specifically the compound of formula I may be converted to a 1:1 mixture of diastereomeric amides by treating with chiral amines, aminoacids, aminoalcohols derived from aminoacids; conventional reaction conditions may be employed to convert acid into an amide; the diastereomers may be separated either by fractional crystallization or chromatography and the stereoisomers of compound of formula I may be pre-pared by hydrolysing the pure diastereomeric amide.

Various polymorphs of compound of general formula I forming part of this invention may be prepared by crystallization of compound of formula I under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe nmr spectroscopy, ir spectroscopy, differential scanning calorimetry, powder X-ray diffraction or such other techniques.

The compounds of the present invention may form solvates with standard low molecular weight solvents using methods well known to the person skilled in the art. Such solvates are also contemplated as being within the scope of the present invention. Examples of solvates are the hydrates, which the present compounds are able to form.

The invention also encompasses prodrugs of the present compounds, which on administration undergo chemical conversion by metabolic processes before becoming active pharmacological substances. In general, such prodrugs will be functional derivatives of the present compounds, which are readily convertible in vivo into the required compound of the formula (I). Conventional procedures for the selection and preparation of suitable prodrug derivatives are described, for example, in "Design of Prodrugs", ed. H. Bundgaard, Elsevier, 1985.

The invention also encompasses active metabolites of the present compounds.

The invention also relates to pharmaceutical compositions comprising, as an active ingredient, at least one compound of the formula I or any optical or geometric isomer or tautomeric form thereof including mixtures of these or a pharmaceutically acceptable salt thereof together with one or more pharmaceutically acceptable carriers or diluents.

The invention also provides novel compounds of the formula I for use in therapy.

In an aspect, the present invention provides novel compounds or pharmaceutically acceptable salts thereof that are useful as PPAR-δ activators.

In another aspect, the present invention provides novel compounds that improves mitochondrial energy output.

In another aspect, the present invention provides novel pharmaceutical compositions comprising a pharmaceutically acceptable carrier and a therapeutically effective amount of at least one of the compounds of the present invention or a pharmaceutically acceptable salt thereof.

In another aspect, the present invention relates to a method of treating and/or preventing Type I or Type II diabetes.

In a still further aspect, the present invention relates to the use of one or more compounds of the general formula I or pharmaceutically acceptable salts thereof for the preparation of a pharmaceutical composition for the treatment and/or prevention of Type I or Type II diabetes.

In a still further aspect, the present compounds are useful for the treatment and/or prevention of IGT.

In a still further aspect, the present compounds are useful for the treatment and/or prevention of Type 2 diabetes.

In a still further aspect, the present compounds are useful for the delaying or prevention of the progression from IGT to Type 2 diabetes.

In a still further aspect, the present compounds are useful for the delaying or prevention of the progression from non-insulin requiring Type 2 diabetes to insulin requiring Type 2 diabetes.

In another aspect, the present compounds reduce blood glucose and triglyceride levels and are accordingly useful for the treatment and/or prevention of ailments and disorders such as diabetes and/or obesity.

In still another aspect, the present compounds are useful for the treatment and/or prophylaxis of insulin resistance (Type 2 diabetes), impaired glucose tolerance, dyslipidemia, disorders related to Syndrome X such as hypertension, obesity, insulin resistance, hyperglycaemia, atherosclerosis, artherosclerosis, hyperlipidemia, coronary artery disease, myocardial ischemia and other cardiovascular disorders.

In still another aspect, the present compounds are useful for the treatment and/or prophylaxis of diseases or complications related to atherosclerosis such as coronary artery diseases, coronary heart diseases, heart attack, myocardial infarct, coronary infarct, transient ischemic attack (TIA) or stroke.

In still another aspect, the present compounds are effective in decreasing apoptosis in mammalian cells such as beta cells of Islets of Langerhans.

In still another aspect, the present compounds are useful for the treatment of certain renal diseases including glomerulonephritis, glomerulosclerosis, nephrotic syndrome, hypertensive nephrosclerosis.

In still another aspect, the present compounds may also be useful for improving cognitive functions in dementia, treating diabetic complications, psoriasis, polycystic ovarian syndrome (PCOS) and prevention and treatment of bone loss, e.g. osteoporosis.

In yet another aspect, the invention also relates to the use of the present compounds, which after administration lower the bio-markers of atherosclerosis like, but not limited to, c-reactive protein (CRP), TNFα and IL-6.

The present compounds may also be administered in combination with one or more further pharmacologically active substances e.g., selected from antiobesity agents, antidiabetics, antihypertensive agents, agents for the treatment and/or prevention of complications resulting from or associated with diabetes and agents for the treatment and/or prevention of complications and disorders resulting from or associated with obesity.

Thus, in a further aspect of the invention the present compounds may be administered in combination with one or more antiobesity agents or appetite regulating agents.

Such agents may be selected from the group consisting of CART (cocaine amphetamine regulated transcript) agonists, NPY (neuropeptide Y) antagonists, MC4 (melanocortin 4) agonists, orexin antagonists, TNF (tumor necrosis factor)

agonists, CRF (corticotropin releasing factor) agonists, CRF BP (corticotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators or TR β agonists.

In one embodiment of the invention the antiobesity agent is leptin.

In another embodiment the antiobesity agent is dexamphetamine or amphetamine.

In another embodiment the antiobesity agent is fenfluramine or dexfenfluramine.

In still another embodiment the antiobesity agent is sibutramine.

In a further embodiment the antiobesity agent is orlistat.

In another embodiment the antiobesity agent is mazindol or phentermine.

Suitable antidiabetics comprise insulin, GLP-1 (glucagon like peptide-1) derivatives such as those disclosed in WO 98/08871 to Novo Nordisk A/S, which is incorporated herein by reference as well as orally active hypoglycaemic agents.

The orally active hypoglycaemic agents preferably comprise sulphonylureas, biguanides, meglitinides, glucosidase inhibitors, glucagon antagonists such as those disclosed in WO 99/01423 to Novo Nordisk A/S and Agouron Pharmaceuticals, Inc., GLP-1 agonists, potassium channel openers such as those disclosed in WO 97/26265 and WO 99/03861 to Novo Nordisk A/S which are incorporated herein by reference, DPP-IV (dipeptidyl peptidaseIV) inhibitors, inhibitors of hepatic enzymes involved in stimulation of gluconeogenesis and/or glycogenolysis, glucose uptake modulators, compounds modifying the lipid metabolism such as antihyperlipidemic agents and antilipidemic agents as HMG CoA inhibitors (statins), compounds lowering food intake, RXR agonists and agents acting on the ATP-dependent potassium channel of the β-cells.

In one embodiment of the invention the present compounds are administered in combination with insulin.

In a further embodiment the present compounds are administered in combination with a sulphonylurea e.g. tolbutamide, glibenclamide, glipizide or glicazide.

In another embodiment the present compounds are administered in combination with a biguanide e.g. metformin.

In yet another embodiment the present compounds are administered in combination with a meglitinide e.g. repaglinide or senaglinide.

In a further embodiment the present compounds are administered in combination with an α-glucosidase inhibitor e.g. miglitol or acarbose.

In another embodiment the present compounds are administered in combination with an agent acting on the ATP-dependent potassium channel of the β-cells e.g. tolbutamide, glibenclamide, glipizide, glicazide or repaglinide.

Furthermore, the present compounds may be administered in combination with nateglinide.

In still another embodiment the present compounds are administered in combination with an antihyperlipidemic agent or antilipidemic agent e.g. cholestyramine, colestipol, clofibrate, gemfibrozil, fenofibrate, bezafibrate, tesaglitazar, EML-4156, LY-518674, LY-519818, MK-767, atorvastatin, fluvastatin, lovastatin, pravastatin, simvastatin, cerivastin, acipimox, ezetimibe probucol, dextrothyroxine or nicotinic acid.

In yet another embodiment the present compounds are administered in combination with a thiazolidinedione e.g. troglitazone, ciglitazone, pioglitazone or rosiglitazone.

In a further embodiment the present compounds are administered in combination with more than one of the above-mentioned compounds e.g. in combination with a sulphonylurea and metformin, a sulphonylurea and acarbose, repaglinide and metformin, insulin and a sulphonylurea, insulin and metformin, insulin, insulin and lovastatin, etc.

Furthermore, the present compounds may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19$^{th}$ Edition, Gennaro, Ed., Mack Publishing Co., Easton, Pa., 1995.

It should be understood that any suitable combination of the compounds according to the invention with one or more of the above-mentioned compounds and optionally one or more further pharmacologically active substances are considered to be within the scope of the present invention.

The present invention also relates to a process for the preparation of the above said novel compounds, their derivatives, their analogs, their tautomeric forms, their stereoisomers, their polymorphs, their pharmaceutically acceptable salts or pharmaceutically acceptable solvates.

Pharmaceutical Compositions

The compounds of the invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995. The compositions may appear in conventional forms, for example capsules, tablets, aerosols, solutions, suspensions or topical applications.

Typical compositions include a compound of formula I or a pharmaceutically acceptable acid addition salt thereof, associated with a pharmaceutically acceptable excipient which may be a carrier or a diluent or be diluted by a carrier, or enclosed within a carrier which can be in the form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, peanut oil, olive oil, gelatine, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, salt for influencing osmotic pressure, buffers and/or colouring substances and the like, which do not deleteriously react with the active compounds.

The route of administration may be any route, which effectively transports the active compound to the appropriate or desired site of action, such as oral, nasal, pulmonary, transdermal or parenteral e.g. rectal, depot, subcutaneous, intravenous, intraurethral, intramuscular, intranasal, ophthalmic solution or an ointment, the oral route being preferred.

If a solid carrier is used for oral administration, the preparation may be tabletted, placed in a hard gelatin capsule in powder or pellet form or it can be in the form of a troche or lozenge. If a liquid carrier is used, the preparation may be in the form of a syrup, emulsion, soft gelatin capsule or sterile injectable liquid such as an aqueous or non-aqueous liquid suspension or solution.

For nasal administration, the preparation may contain a compound of formula I dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet which may be prepared by conventional tabletting techniques may contain:

| Core: | |
|---|---|
| Active compound (as free compound or salt thereof) | 5 mg |
| Colloidal silicon dioxide (Aerosil) | 1.5 mg |
| Cellulose, microcryst. (Avicel) | 70 mg |
| Modified cellulose gum (Ac-Di-Sol) | 7.5 mg |
| Magnesium stearate | Ad. |
| Coating: | |
| HPMC approx. | 9 mg |
| *Mywacett 9-40 T approx. | 0.9 mg |

*Acylated monoglyceride used as plasticizer for film coating.

If desired, the pharmaceutical composition of the invention may comprise the compound of formula (I) in combination with further pharmacologically active substances such as those described in the foregoing.

The compounds of the invention may be administered to a mammal, especially a human in need of such treatment, prevention, elimination, alleviation or amelioration of diseases related to the regulation of blood sugar.

Such mammals include also animals, both domestic animals, e.g. household pets, and non-domestic animals such as wildlife.

The compounds of the invention are effective over a wide dosage range. A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain of from 0.05 to about 1000 mg, preferably from about 0.1 to about 500 mg, and more preferred from about 0.5 mg to about 200 mg.

Any novel feature or combination of features described herein is considered essential to this invention.

EXAMPLES

The following examples and general procedures refer to intermediate compounds and final products identified in the specification and in the synthesis schemes. The preparation of the compounds of the present invention is described in detail using the following examples. Occasionally, the reaction may not be applicable as described to each compound included within the disclosed scope of the invention. The compounds for which this occurs will be readily recognised by those skilled in the art. In these cases the reactions can be successfully performed by conventional modifications known to those skilled in the art, that is, by appropriate protection of interfering groups, by changing to other conventional reagents, or by routine modification of reaction conditions. Alternatively, other reactions disclosed herein or otherwise conventional will be applicable to the preparation of the corresponding compounds of the invention. In all preparative methods, all starting materials are known or may easily be prepared from known starting materials. The structures of the compounds are confirmed nuclear magnetic resonance (NMR). NMR shifts (6) are given in parts per million (ppm. Mp is melting point and is given in OC.

The abbreviations as used in the examples have the following meaning:

THF: tetrahydrofuran

DMSO: dimethylsulfoxide $CDCl_3$: deutorated chloroform

DMF: N,N-dimethylformamide min: minutes h: hours

General procedure (A)
Step A:
  Reacting a compound of formula (II)

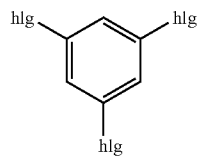

wherein hlg is halogen, with a compound of formula (III)

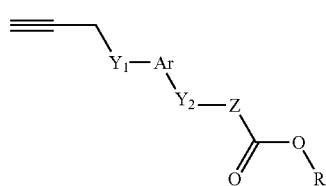

wherein Ar, $Y_1$, $Y_2$, Z and R are as defined above, using Sonogashira reaction conditions to give a compound of formula (IV)

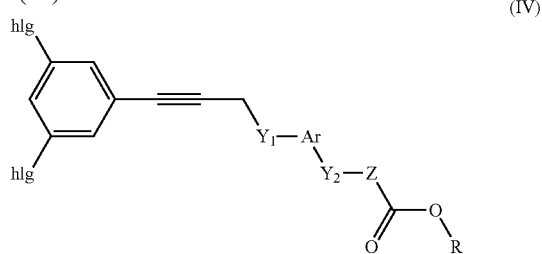

wherein hlg, Ar, $Y_1$, $Y_2$, Z and R are as defined above except that R is not hydrogen.
Step B:
  Reacting a compound of formula (IV), wherein hlg, Ar, $Y_1$, $Y_2$, Z and R are as defined above except that R is not hydrogen, with a compound of formula (V)

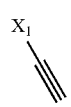

wherein $X_1$ is a defined above, using Sonogashira reaction conditions to give a compound of formula (VI)

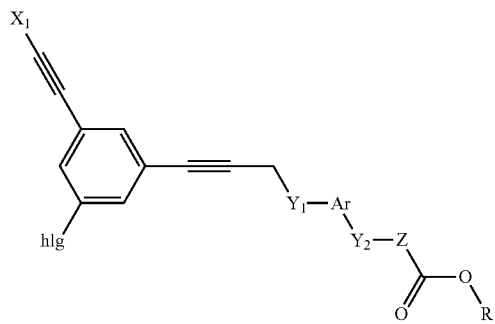

wherein hlg, Ar, $Y_1$, $Y_2$, Z. $X_1$ and R are as defined above except that R is not hydrogen.
Step C:
  Reacting a compound of formula (VI), wherein hlg, Ar, $Y_1$, $Y_2$, Z. $X_1$ and R are as defined above except that R is not hydrogen, with $X_2$, where $X_2$ is defined as described above, using appropriate coupling conditions to give a compound of formula (I), wherein Ar, $Y_1$, $Y_2$, Z, $X_1$, $X_2$ and R are as defined above except that R is not hydrogen.
Step D:
  By chemical or enzymatic saponification of a compound of formula I wherein Ar, $Y_1$, $Y_2$, Z $X_1$, $X_2$ and R are as defined above except that R is not hydrogen, to give a compound of formula wherein Ar, $Y_1$, $Y_2$, Z $X_1$, $X_2$ and R are as defined above, except that R is hydrogen.
General Procedure (B)
  The order in which formula (II) is reacted with the compounds of formula (III), (V) and $X_2$, step A-C in general procedure A, can be changed.
Intermediate 1

(2-Methyl-4-prop-2-ynyloxy-phenoxy)-acetic acid methyl ester

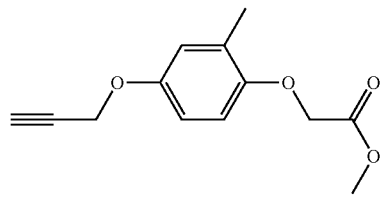

To a solution of (4-hydroxy-2-methyl-phenoxy)-acetic acid methyl ester (5.1 g, 25.8 mmol) and K2CO3 (7.1 g, 51.5 mmol) in acetone (85 ml) was added propagylbromide (3.1 g, 25.7 mmol) at room temperature. The reaction mixture was stirred at room temperature for 2 days, and then filtered and evaporated in vacuo. The residue was purified on column chromatography using methylene chloride as eluent to give the title compound in 6.0 (100%) yield.
$^1$H NMR (CDCl$_3$): δ 2.29 (3H, s), 2.50 (1H, t), 3.80 (3H, s), 4.60 (2H, s), 4.62 (2H, d), 6.63-6.84 (3H, m).
Intermediate 2

{4-[3-(3,5-Dibromo-phenyl)-prop-2-ynyloxy]-2-methyl-phenoxy}-acetic acid

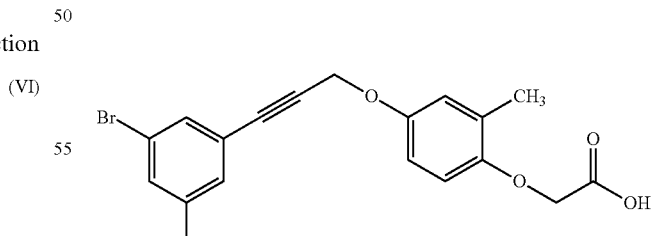

A solution of 1,3,5-tribromophenyl (4.12 g, 13.1 mmol), (2-methyl-4-prop-2-ynyloxyphenoxy)-acetic acid methyl ester (4.6 g, 19.6 mmol, intermediate 1), Pd(PPh$_3$)$_4$ (1.5 g, 1.3 mmol) and CuI (0.7 g, 3.7 mmol) in triethylamine (200 ml) was heated in a sealed tube in a microwave own at 65° C. for 30 min. The reaction mixture was filtered and the filtrate was evaporated. The residue was purified on column chromatography using methylene chloride as eluent to give {4-[3-(3,5-dibromo-phenyl)-prop-2-ynyloxy]-2-methyl-phenoxy}-acetic acid methyl ester in 1.18 g (52%) yield. ¹H NMR (CDCl₃): δ 2.99 (3H, s), 3.82 (2H, s), 4.63 (2H, s), 4.83 (2H, s), 6.77-6.86 (3H, m), 7.50 (2H, m), 7.64 (1H, m).

A solution of {4-[3-(3,5-dibromo-phenyl)-prop-2-ynyloxy]-2-methyl-phenoxy}-acetic acid methyl ester (207 mg, 0.44 mmol) in ethanol (50 ml) and 1N NaOH (5 ml) was stirred at 75° C. for 30 min. The reaction mixture was evaporated and the residue dissolved in water (10 ml). Aqueous 1N HCl (5 ml) was added and the mixture was extracted with methylene chloride (3×10 ml). The combined organic phases were dried and evaporated to give the title compound in 187 mg (93%) yield.

¹H NMR (CDCl₃): δ 2.28 (3H, s), 4.65 (2H, s), 4.84 (2H, s), 6.65-6.87 (3H, m), 7.49 (2H, m), 7.64 (1H, m).

Intermediate 3

1,3-Dibromo-5-phenylethynyl-benzene

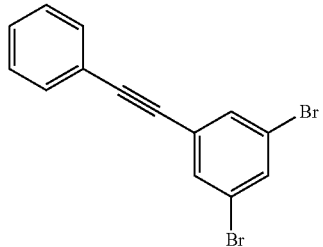

To a solution of 1,3,5-tribromophenyl (2.7 g, 8.5 mmol), Pd(PPh₃)₄ (0.8 g, 0.7 mmol) and CuI (0.7 g, 3.6 mmol) in diisopropulamine (42 ml) was added dropwise a solution of phenylacetylene (1.7 g, 17.0 mmol) in diisoprolylamine (21 ml) under nitrogen atmosphere. The reaction mixture was stirred at 60° C. for 6 hours, and filtered through filter-aid. The filtrate was evaporated and residue was purified on column chromatography using heptane as eluent to give the title compound in 1.5 g (52%) yield.

¹H NMR (CDCl₃): δ 7.34-7.65 (8H, m).

Example 1

{4-[3-(3-Bromo-5-phenylethynyl-phenyl)-prop-2-ynyloxy]-phenoxy}-acetic acid

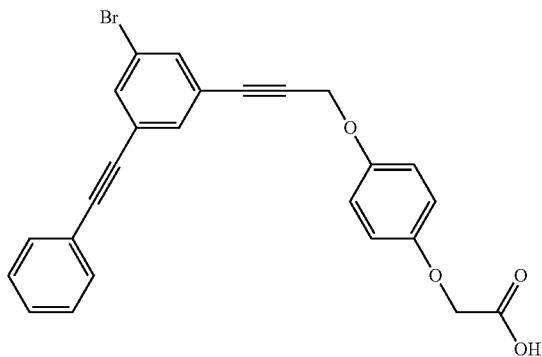

A mixture of 1,3-dibromo-5-phenylethynyl-benzene (0.1 g, 0.3 mmol, intermediate 3), (4-prop-2-ynyloxy-phenoxy)-acetic acid methyl ester (66 mg, 0.3 mmol), Pd(PPh₃)₂Cl₂ (10 mg, 0.015 mmol), CuI (16 mg, 0.008 mmol) in dry DMF (1.5 ml) and triethylamine (1.5 ml) was heated in a microwave own for 10 min at 70° C. in a sealed tube. The reaction mixture was filtered through Decalite and the filtrate was evaporated. The residue was purified on column chromatography to give {4-[3-(3-bromo-5-phenylethynyl-phenyl)-prop-2-ynyloxy]-phenoxy}-acetic acid methyl ester in 27 mg (20%) yield.

¹H NMR (CDCl₃): δ 3.80 (3H, s), 4.61 (2H, s), 4.85 (2H, s), 6.85-6.99 (4H, m), 7.36 (3H, m), 7.50 (4H, m), 7.63 (1H, m).

To a solution of {4-[3-(3-bromo-5-phenylethynyl-phenyl)-prop-2-ynyloxy]-phenoxy}-acetic acid methyl ester (66 mg, 0.14 mmol) in THF (1.5 ml) and methanol (0.3 ml) was added a ice-cold solution of LiOH (1 M, 2 ml). The reaction mixture was stirred at 0° C. for 45 min., after which water (10 ml) and aqueous HCl (1M, 2 ml) were added. The mixture was extracted with ethyl acetate (2×5 ml), and the combined organic phases were dried and evaporated to give the title compound in 64 mg (100%) yield.

¹H NMR (CDCl₃): δ 4.65 (2H, s), 4.87 (2H, s), 6.87-7.00 (4H, m), 7.36 (3H, m), 7.51 (4H, m), 7.63 (1H, m).

Example 2

{4-[3-(3,5-Bis-phenylethynyl-phenyl)-prop-2-ynyloxy]-phenoxy}-acetic acid

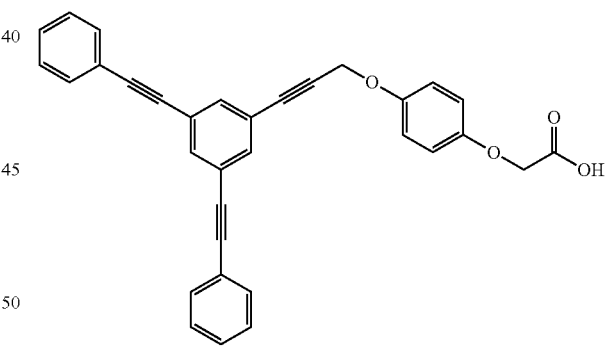

A solution of phenylacetylene (0.20 g, 1.98 mmol), {4-[3-(3,5-dibromo-phenyl)-prop-2-ynyloxy]-phenoxy}-acetic acid methyl ester (0.3 g, 0.66 mmol), Pd(PPh₃)₄ (0.11 g, 0.1 mmol) and CuI (0.05 g, 0.26 mmol) in triethylamine (10 ml) was heated in a sealed tube in a microwave own at 65° C. for 1 hour. The reaction mixture was filtered and the filtrate was evaporated. The residue was purified on HPLC using acetonitril/water as eluent to give {4-[3-(3,5-bis-phenylethynyl-phenyl)-prop-2-ynyloxy]-phenoxy}-acetic acid methyl ester in 150 mg (46%) yield.

¹H NMR (CDCl₃): δ 3.79 (3H, s), 4.60 (2H, s), 4.85 (2H, s), 6.85-7.00 (4H, m), 7.35 (6H, m), 7.54 (6H, m), 7.64 (1H, m).

To a solution of {4-[3-(3,5-bis-phenylethynyl-phenyl)-prop-2-ynyloxy]-phenoxy}-acetic acid methyl ester (0.26 g, 0.51 mmol) in THF (5.6 ml) and methanol (1.1 ml) was added a ice-cold solution of LiOH (1 M, 5.6 ml). The reaction mixture was stirred at 0° C. for 45 min., after which water (37 ml) and aqueous HCl (1M, 7.5 ml) were added. The mixture was extracted with ethyl acetate (2×25 ml), and the combined organic phases were dried and evaporated to give the title compound in 240 mg (96%) yield.

$^1$H NMR (CDCl3): δ 4.65 (2H, s), 4.87 (2H, s), 6.85-7.04 (4H, m), 7.35 (6H, m), 7.53 (6H, m), 7.64 (1H, m).

Example 3

(4-{3-[3-Bromo-5-(3-piperidin-1-yl-prop-1-ynyl)-phenyl]-prop-2-ynyloxy}-2-methyl-phenoxy)-acetic acid

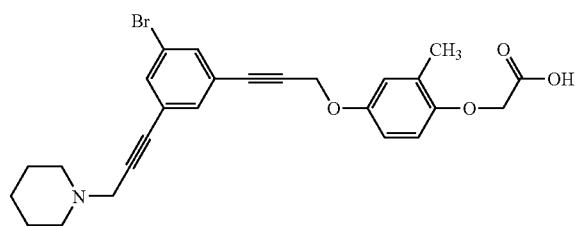

A mixture of 1-prop-2-ynyl-piperidine (53 mg, 0.44 mmol), {4-[3-(3,5-dibromo-phenyl)-prop-2-ynyloxy]-2-methyl-phenoxy}-acetic acid methyl ester (204 mg, 0.44 mmol, intermediate 2), Pd(PPh$_3$)$_4$ (50 mg, 0.044 mmol), CuI (23 mg, 0.12 mmol) in dry DMF (2 ml) and triethylamine (2 ml) was heated in a microwave own for 30 min at 60° C. in a sealed tube. The reaction mixture was filtered through Decalite and the filtrate was evaporated. The residue was purified on column chromatography using ethyl acetate/methanol mixtures to give (4-{3-[3-bromo-5-(3-piperidin-1-yl-prop-1-ynyl)-phenyl]-prop-2-ynyloxy}-2-methyl-phenoxy)-acetic acid methyl ester in 105 mg (47%) yield.

$^1$H NMR (CDCl$_3$): δ 1.38-1.70 (6H, m), 2.30 (3H, s), 2.55 (4H, br.s), 3.47 (2H, s), 3.79 (3H, s), 4.62 (2H, s), 4.83 (2H, s), 6.65-6.87 (3H, m), 7.38-7.54 (3H, m).

A solution of (4-{3-[3-bromo-5-(3-piperidin-1-yl-prop-1-ynyl)-phenyl]-prop-2-ynyloxy}-2-methyl-phenoxy)-acetic acid methyl ester (45 mg, 0.088 mmol) in ethanol (5 ml) and 1N NaOH (0.5 ml) was stirred at 75° C. for 30 min. The reaction mixture was evaporated and the residue dissolved in water (2 ml). Aqueous 1N HCl (0.5 ml) was added and the mixture was extracted with methylene chloride (3×15 ml). The combined organic phases were dried and evaporated to give the title compound in 36 mg (88%) yield.

$^1$H NMR (CDCl$_3$): δ 1.48-1.95 (3H, m), 2.10-2.27 (3H, m), 2.27 (3H, s), 2.98 (2H, m), 3.54 (2H, m), 4.15 (2H, s), 4.60 (2H, s), 4.82 (2H, s), 6.67-6.84 (3H, m), 7.40-7.58 (3H, m).

Example 4

(2-Methyl-4-{3-[3-(3-piperidin-1-yl-prop-1-ynyl)-5-(4-trifluoromethyl-phenylethynyl)-phenyl]-prop-2-ynyloxy}-phenoxy)-acetic acid

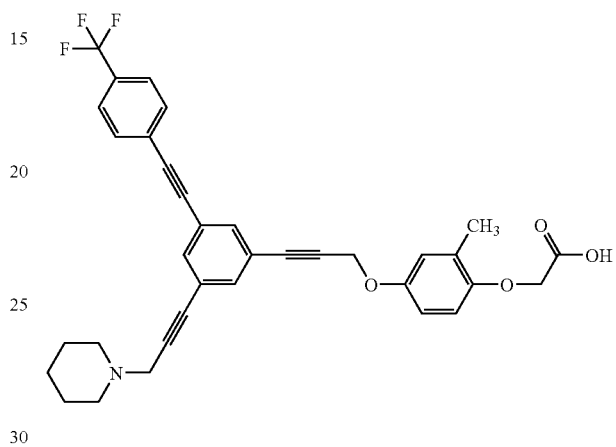

A mixture of 1-ethynyl-4-trifluoromethyl-benzene (300 mg, 1.77 mmol), (4-{3-[3-bromo-5-(3-piperidin-1-yl-prop-1-ynyl)-phenyl]-prop-2-ynyloxy}-2-methyl-phenoxy)-acetic acid methyl ester (100 mg, 0.2 mmol, example 3), Pd(PPh$_3$)$_4$ (22 mg, 0.02 mmol), CuI (10 mg, 0.055 mmol) in dry DMF (2 ml) and triethylamine (2 ml) was heated in a microwave own for 50 min at 60° C. in a sealed tube. The reaction mixture was filtered through Decalite and the filtrate was evaporated. The residue was purified on column chromatography using ethyl acetate/methanol mixtures to give (2-methyl-4-{3-[3-(3-piperidin-1-yl-prop-1-ynyl)-5-(4-trifluoromethyl-phenylethynyl)-phenyl]-prop-2-ynyloxy}-phenoxy)-acetic acid methyl ester in 30 mg (26%) yield.

$^1$H NMR (CDCl$_3$): δ 1.46 (2H, m), 1.64 (4H, m), 2.30 (3H, s), 2.56 (4H, m), 3.48 (2H, s), 3.60 (3H, s), 4.62 (2H, s), 4.84 (2H, s), 6.65-6.87 (3H, m), 7.45-7.64 (7H, m).

A solution of (2-methyl-4-{3-[3-(3-piperidin-1-yl-prop-1-ynyl)-5-(4-trifluoromethylphenylethynyl)-phenyl]-prop-2-ynyloxy}-phenoxy)-acetic acid methyl ester (30 mg, 0.05 mmol) in ethanol (1 ml) and 1N NaOH (0.25 ml) was stirred at 75° C. for 30 min. The reaction mixture was evaporated and the residue dissolved in water (2 ml). Aqueous 1N HCl (0.25 ml) was added and the mixture was extracted with methylene chloride (2×10 ml). The combined organic phases were dried and evaporated to give the title compound in 25 mg (86%) yield.

$^1$H NMR (CDCl$_3$): δ 1.50-2.15 (6H, m), 2.27 (3H, s), 2.90-3.50 (4H, m), 4.10 (2H, s), 4.56 (2H, s), 4.83 (2H, s), 6.67-6.85 (3H, m), 7.43-7.65 (7H, m).

Example 5

(4-{3-[3,5-Bis-(3-piperidin-1-yl-prop-1-ynyl)-phenyl]-prop-2-ynyloxy}-2-methyl-phenoxy)-acetic acid

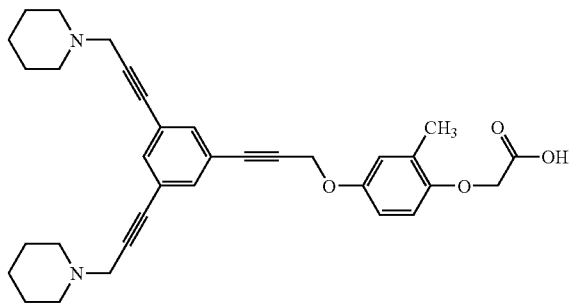

A mixture of 1-prop-2-ynyl-piperidine (322 mg, 2.62 mmol), (4-{3-[3-bromo-5-(3-piperidin-1-yl-prop-1-ynyl)-phenyl]-prop-2-ynyloxy}-2-methyl-phenoxy)-acetic acid methyl ester (204 mg, 0.4 mmol, example 3), Pd(PPh$_3$)$_4$ (50 mg, 0.044 mmol), CuI (23 mg, 0.122 mmol) in dry DMF (2 ml) and triethylamine (2 ml) was heated in a microwave own for 30 min at 60° C. in a sealed tube. The reaction mixture was filtered through Decalite and the filtrate was evaporated. The residue was purified on column chromatography using ethyl acetate/methanol mixtures to give (4-{3-[3,5-bis-(3-piperidin-1-yl-prop-1-ynyl)-phenyl]-prop-2-ynyloxy}-2-methyl-phenoxy)-acetic acid methyl ester in 138 mg (57%) yield.

$^1$H NMR (CDCl$_3$): δ 1.36-1.74 (12H, m), 2.99 (3H, s), 2.40-2.65 (8H, m), 3.36 (2H, s), 3.79 (2H, s), 4.62 (2H, s), 4.84 (2H, s), 6.65-6.87 (3H, m), 7.44 (3H, m).

A solution of (4-{3-[3,5-bis-(3-piperidin-1-yl-prop-1-ynyl)-phenyl]-prop-2-ynyloxy}-2-methyl-phenoxy)-acetic acid methyl ester (126 mg, 0.247 mmol) in ethanol (5 ml) and 1N NaOH (0.5 ml) was stirred at 75° C. for 30 min. The reaction mixture was evaporated and the residue dissolved in water (2 ml). Aqueous 1N HCl (0.5 ml) was added and the mixture was extracted with methylene chloride (3×15 ml). The combined organic phases were dried and evaporated to give the title compound in 115 mg (93%) yield.

$^1$H NMR (CDCl$_3$): δ 1.40-1.82 (12H, m), 2.32 (3H, s), 2.64-2.92 (8H, m), 3.66 (4H, s), 4.57 (2H, s), 4.81 (2H, s), 6.74-6.86 (3H, m), 7.30-7.40 (3H, m).

Example 6

(4-{3-[3-Bromo-5-(3-morpholin-4-yl-prop-1-ynyl)-phenyl]-prop-2-ynyloxy}-2-methyl-phenoxy)-acetic acid

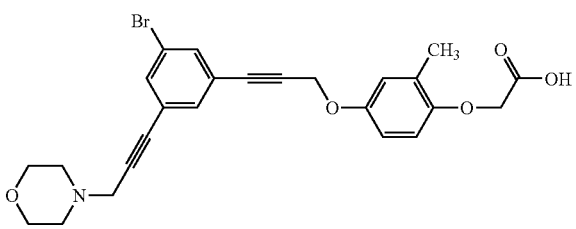

A mixture of 4-prop-2-ynyl-morpholine (330 mg, 2.64 mmol), {4-[3-(3,5-dibromophenyl)-prop-2-ynyloxy]-2-methyl-phenoxy}-acetic acid methyl ester (206 mg, 0.44 mmol, intermediate 2), Pd(PPh$_3$)$_2$Cl$_2$ (50 mg, 0.044 mmol), CuI (23 mg, 0.123 mmol) in dry DMF (2 ml) and triethylamine (2 ml) was heated in a microwave own for 30 min at 60° C. in a sealed tube. The reaction mixture was filtered through Decalite and the filtrate was evaporated. The residue was purified on column chromatography using methylene chloride/THF mixtures to give (4-{3-[3-bromo-5-(3-morpholin-4-yl-prop-1-ynyl)-phenyl]-prop-2-ynyloxy}-2-methylphenoxy)-acetic acid methyl ester in 130 mg (58%) yield.

$^1$H NMR (CDCl$_3$): δ 2.29 (3H, s), 2.63 (4H, t), 3.50 (2H, s), 3.77 (4H, t), 3.78 (3H, s), 4.61 (2H, s), 4.83 (2H, s), 6.65-6.85 (3H, m), 7.25-7.73 (3H, m).

A solution of (4-{3-[3-bromo-5-(3-morpholin-4-yl-prop-1-ynyl)-phenyl]-prop-2-ynyloxy}-2-methyl-phenoxy)-acetic acid methyl ester (45 mg, 0.088 mmol) in ethanol (5 ml) and 1N NaOH (0.5 ml) was stirred at 75° C. for 30 min. The reaction mixture was evaporated and the residue dissolved in water (2 ml). Aqueous 1N HCl (0.6 ml) was added and the mixture was extracted with methylene chloride (3×15 ml). The combined organic phases were dried and evaporated to give the title compound in 44 mg (99%) yield.

$^1$H NMR (CDCl$_3$): δ 2.27 (3H, s), 3.24 (4H, m), 4.02 (4H, t), 4.06 (2H, s), 4.58 (2H, s), 4.82 (2H, s), 6.65-6.85 (3H, m), 7.35-7.55 (3H, m).

Example 7

(2-Methyl-4-{3-[3-(3-morpholin-4-yl-prop-1-ynyl)-5-(4-trifluoromethyl-phenylethynyl)-phenyl]-prop-2-ynyloxy}-phenoxy)-acetic acid

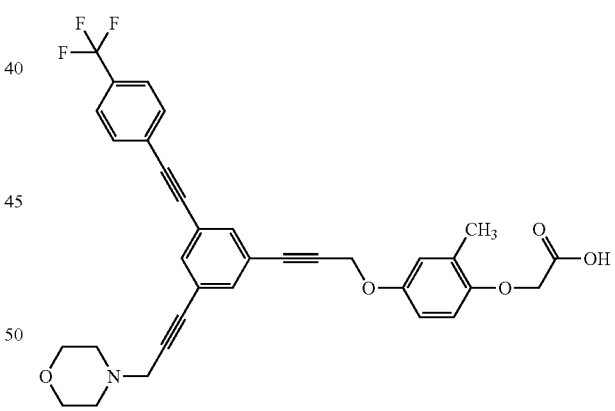

A mixture of 1-ethynyl-4-trifluoromethyl-benzene (159 mg, 0.94 mmol), (4-{3-[3-bromo-5-(3-morpholin-4-yl-prop-1-ynyl)-phenyl]-prop-2-ynyloxy}-2-methyl-phenoxy)-acetic acid methyl ester (160 mg, 0.31 mmol, example 6), Pd(PPh$_3$)$_2$Cl$_2$ (36 mg, 0.031 mmol), CuI (16 mg, 0.087 mmol) in dry DMF (2 ml) and triethylamine (2 ml) was heated in a microwave own for 1 hour at 60° C. in a sealed tube. The reaction mixture was filtered through Decalite and the filtrate was evaporated. The residue was purified on column chromatography using ethyl acetate/methanol mixtures to give (2-methyl-4-{3-[3-(3-morpholin-4-yl-prop-1-ynyl)-5-(4-trifluoromethyl-phenylethynyl)-phenyl]-prop-2-ynyloxy}-phenoxy)-acetic acid methyl ester in 18 mg (10%) yield.

$^1$H NMR (CDCl$_3$): δ 2.31 (3H, s), 2.64 (4H, t), 3.53 (2H s), 3.77 (4H, t), 3.79 (3H, s), 4.63 (2H, s), 4.85 (2H, s), 6.65-6.87 (3H, m), 7.45-7.64 (7H, m).

To a solution of (2-methyl-4-{3-[3-(3-morpholin-4-yl-prop-1-ynyl)-5-(4-trifluoromethylphenylethynyl)-phenyl]-prop-2-ynyloxy}-phenoxy)-acetic acid methyl ester (0.26 g, 0.51 mmol) in THF (5.3 ml) and methanol (1 ml) was added a ice-cold solution of LiOH (1 M, 5.3 ml). The reaction mixture was stirred at 0° C. for 45 min., after which water (10 ml) and aqueous HCl (1M, 7.4 ml) were added. The mixture was extracted with ethyl acetate (2×80 ml), and the combined organic phases were dried and evaporated to give the title compound in 272 mg (94%) yield.

$^1$H NMR (CDCl3): δ 2.29 (3H, s), 3.13 (4H, br. s), 3.93 (2H, s), 3.99 (4H, t), 4.63 (2H, s), 4.84 (2H, s), 6.70-6.88 (3H, m), 7.35-7.64 (7H, m).

Example 8

(2-Methyl-4-{3-[3-(3-morpholin-4-yl-prop-1-ynyl)-5-phenylethynyl-phenyl]-prop-2-ynyloxy}-phenoxy)-acetic acid

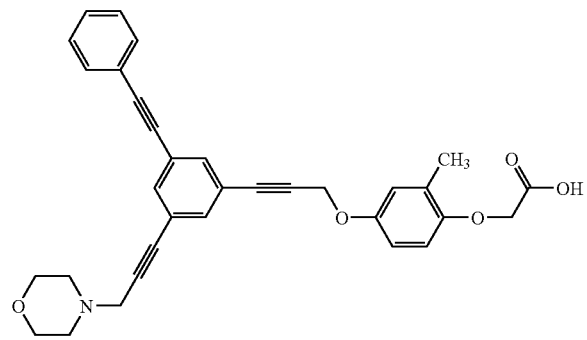

A mixture of phenylacetylene (169 mg, 1.66 mmol), (4-{3-[3-bromo-5-(3-morpholin-4-yl-prop-1-ynyl)-phenyl]-prop-2-ynyloxy}-2-methyl-phenoxy)-acetic acid methyl ester (100 mg, 0.195 mmol, example 6), Pd(PPh$_3$)$_2$Cl$_2$ (22 mg, 0.02 mmol), CuI (10 mg, 0.055 mmol) in dry DMF (2 ml) and triethylamine (2 ml) was heated in a microwave own for 1 hour at 60° C. in a sealed tube. The reaction mixture was filtered through Decalite and the filtrate was evaporated. The residue was purified on column chromatography using methylene chloride/THF mixtures to give (2-methyl-4-{3-[3-(3-morpholin-4-yl-prop-1-ynyl)-5-phenylethynylphenyl]-prop-2-ynyloxy}-phenoxy)-acetic acid methyl ester in 70 mg (67%) yield.

$^1$H NMR (CDCl$_3$): δ 2.29 (3H, s), 2.63 (4H, t), 3.51 (2H, s), 3.77 (4H, t), 3.79 (3H, s), 4.61 (2H, s), 4.84 (2H, s), 6.65-6.86 (3H, m), 7.32-7.55 (8H, m).

To a solution of (2-methyl-4-{3-[3-(3-morpholin-4-yl-prop-1-ynyl)-5-phenylethynylphenyl]-prop-2-ynyloxy}-phenoxy)-acetic acid methyl ester (70 mg, 0.13 mmol) in THF (1.25 ml) and methanol (0.25 ml) was added a ice-cold solution of LiOH (1 M, 1.25 ml). The reaction mixture was stirred at 0° C. for 460 min., after which water (10 ml) and aqueous HCl (1M, 1.75 ml) were added. The mixture was extracted with ethyl acetate (2×10 ml), and the combined organic phases were dried and evaporated to give the title compound in 68 mg (100%) yield.

$^1$H NMR (CDCl3): δ 2.29 (3H, s), 2.97 (4H, t), 3.83 (2H, s), 3.89 (4H, t), 4.59 (2H, s), 4.82 (2H, s), 6.67-6.85 (3H, m), 7.31-7.54 (8H, m).

Example 9

(4-{3-[3-(4-Chloro-phenylethynyl)-5-(3-morpholin-4-yl-prop-1-ynyl)-phenyl]-prop-2-ynyloxy}-2-methyl-phenoxy)-acetic acid

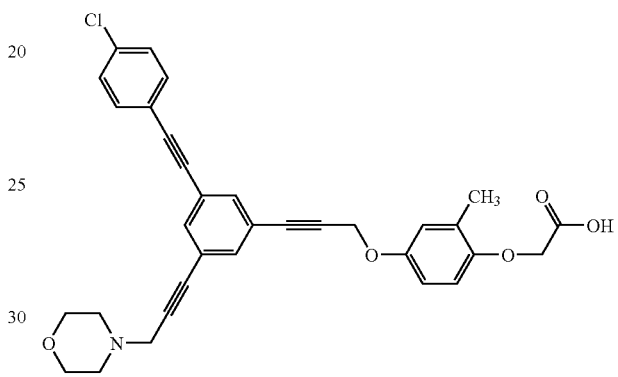

A mixture of 1-chloro-4-ethynyl-benzene (240 mg, 1.76 mmol), (4-{3-[3-bromo-5-(3-morpholin-4-yl-prop-1-ynyl)-phenyl]-prop-2-ynyloxy}-2-methyl-phenoxy)-acetic acid methyl ester (106 mg, 0.207 mmol, example 6), Pd(PPh$_3$)$_4$ (23 mg, 0.021 mmol), CuI (11 mg, 0.058 mmol) in dry DMF (2 ml) and triethylamine (2 ml) was heated in a microwave own for 120 min at 60° C. in a sealed tube. The reaction mixture was filtered through Decalite and the filtrate was evaporated. The residue was purified on column chromatography using methylene chloride/THF mixtures to give (4-{3-[3-(4-chloro-phenylethynyl)-5-(3-morpholin-4-yl-prop-1-ynyl)-phenyl]-prop-2-ynyloxy}-2-methyl-phenoxy)-acetic acid methyl ester in 63 mg (54%) yield.

$^1$H NMR (CDCl$_3$): δ 2.29 (3H, s), 2.63 (4H, t), 3.51 (2H, s), 3.77 (4H, t), 3.79 (3H, s), 4.61 (2H, s), 4.82 (2H, s), 6.65-6.87 (3H, m), 7.29-7.55 (7H, m).

To a solution of (4-{3-[3-(4-chloro-phenylethynyl)-5-(3-morpholin-4-yl-prop-1-ynyl)-phenyl]-prop-2-ynyloxy}-2-methyl-phenoxy)-acetic acid methyl ester (63 mg, 0.11 mmol) in THF (1.25 ml) and methanol (0.25 ml) was added a ice-cold solution of LiOH (1 M, 1.25 ml). The reaction mixture was stirred at 0° C. for 460 min., after which water (10 ml) and aqueous HCl (1M, 1.75 ml) were added. The mixture was extracted with ethyl acetate (2×10 ml), and the combined organic phases were dried and evaporated to give the title compound in 29 mg (48%) yield.

$^1$H NMR (CDCl3): δ 2.29 (3H, s), 2.93 (4H, t), 3.75 (2H, s), 3.89 (4H, t), 4.65 (2H, s), 4.85 (2H, s), 6.67-6.85 (3H, m), 7.31-7.54 (7H, m).

Example 10

(4-{3-[3-(4-Methanesulfonyl-phenylethynyl)-5-(3-morpholin-4-yl-prop-1-ynyl)-phenyl]-prop-2-ynyloxy}-2-methyl-phenoxy)-acetic acid

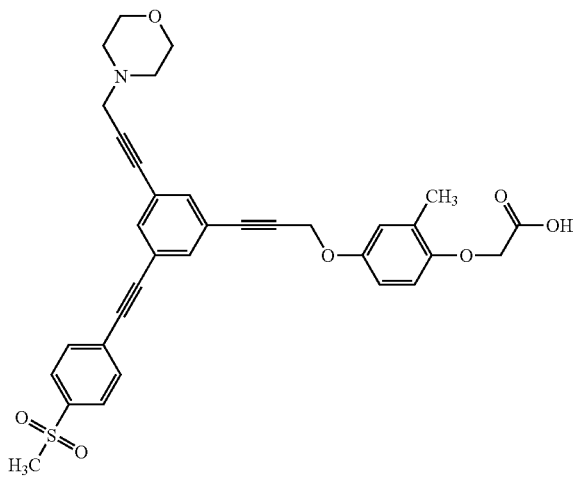

A mixture of 1-ethynyl-4-methanesulfonyl-benzene (346 mg, 1.92 mmol), (4-{3-[3-bromo-5-(3-morpholin-4-yl-prop-1-ynyl)-phenyl]-prop-2-ynyloxy}-2-methyl-phenoxy)-acetic acid methyl ester (123 mg, 0.24 mmol, example 6), Pd(PPh$_3$)$_2$Cl$_2$ (17 mg, 0.024 mmol), CuI (12 mg, 0.067 mmol) in dry DMF (2 ml) and triethylamine (2 ml) was heated in a microwave own for 1 hour at 65° C. in a sealed tube. The reaction mixture was filtered through Decalite and the filtrate was evaporated. The residue was purified on column chromatography using methylene chloride/THF mixtures to give (4-{3-[3-(4-methanesulfonyl-phenylethynyl)-5-(3-morpholin-4-yl-prop-1-ynyl)-phenyl]-prop-2-ynyloxy}-2-methyl-phenoxy)-acetic acid methyl ester in 50 mg (34%) yield.

$^1$H NMR (CDCl$_3$): δ 2.29 (3H, s), 2.65 (4H, t), 3.08 (3H, s), 3.52 (2H, s), 3.77 (4H, t), 3.79 (3H, s), 4.62 (2H, s), 4.84 (2H, s), 6.65-7.00 (3H, m), 7.43-7.97 (7H, m).

To a solution of (4-{3-[3-(4-methanesulfonyl-phenylethynyl)-5-(3-morpholin-4-yl-prop-1-ynyl)-phenyl]-prop-2-ynyloxy}-2-methyl-phenoxy)-acetic acid methyl ester (50 mg, 0.08 mmol) in THF (1.25 ml) and methanol (0.25 ml) was added a ice-cold solution of LiOH (1 M, 1.25 ml). The reaction mixture was stirred at 0° C. for 460 min., after which water (10 ml) and aqueous HCl (1M, 1.75 ml) were added. The mixture was extracted with ethyl acetate (2×10 ml), and the combined organic phases were dried and evaporated to give the title compound in 15 mg (31%) yield.

$^1$H NMR (CDCl3): δ 2.29 (3H, s), 3.07 (3H, s), 3.22 (4H, br. s), 4.04 (2H, s), 4.03 (4H, br. s), 4.60 (2H, s), 4.84 (2H, s), 6.67-6.85 (3H, m), 7.44 (1H, s), 7.57 (2H, s), 7.67 (2H, d), 7.94 (2H, d).

Example 11

(4-{3-[3-Bromo-5-(4-trifluoromethyl-phenylethynyl)-phenyl]-prop-2-ynyloxy}-2-methylphenoxy)-acetic acid

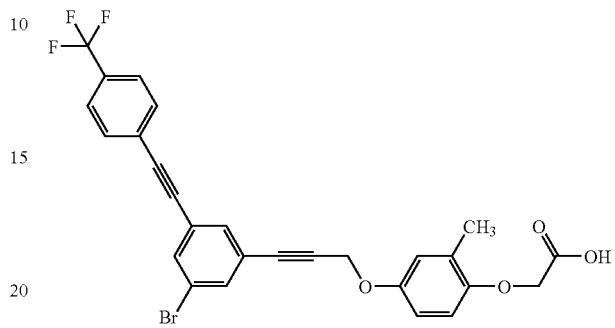

A mixture of 1-ethynyl-4-trifluoromethyl-benzene (149 mg, 0.88 mmol), {4-[3-(3,5-dibromo-phenyl)-prop-2-ynyloxy]-2-methyl-phenoxy}-acetic acid methyl ester (412 mg, 0.88 mmol, intermediate 2), Pd(PPh$_3$)$_2$Cl$_2$ (101 mg, 0.088 mmol), CuI (46 mg, 0.246 mmol) in dry DMF (2 ml) and triethylamine (2 ml) was heated in a microwave own for 20 min. at 75° C. in a sealed tube. The reaction mixture was filtered through Decalite and the filtrate was evaporated. The residue was purified on column chromatography using methylene chloride/heptanes mixtures to give (4-{3-[3-bromo-5-(4-trifluoromethyl-phenylethynyl)-phenyl]-prop-2-ynyloxy}-2-methyl-phenoxy)-acetic acid methyl ester in 94 mg (19%) yield.

$^1$H NMR (CDCl$_3$): δ 2.29 (3H, s), 3.79 (3H, s), 4.62 (2H, s), 4.84 (2H, s), 6.65-6.87 (3H, m), 7.50-7.66 (7H, m).

A solution of (4-{3-[3-bromo-5-(4-trifluoromethyl-phenylethynyl)-phenyl]-prop-2-ynyloxy}-2-methyl-phenoxy)-acetic acid methyl ester (94 mg, 0.169 mmol) in ethanol (5 ml) and 1N NaOH (0.5 ml) was stirred at 75° C. for 30 min. The reaction mixture was evaporated and the residue dissolved in water (2 ml). Aqueous 1N HCl (0.6 ml) was added and the mixture was extracted with methylene chloride (3×15 ml). The combined organic phases were dried and evaporated to give the title compound in 79 mg (86%) yield.

$^1$H NMR (CDCl3): δ 2.29 (3H, s), 4.64 (2H, s), 4.84 (2H, s), 6.65-6.88 (3H, m), 7.48-7.66 (3H, m).

Pharmacological Methods

In Vitro Pparδ Activation Activity

The PPAR transient transactivation assay is based on transient transfection into human HEK293 cells of two plasmids encoding a chimeric test protein and a reporter protein respectively. The chimeric test protein is a fusion of the DNA binding domain (DBD) from the yeast GAL4 transcription factor to the ligand binding domain (LBD) of the human PPAR proteins. The PPAR-LBD moiety harbored in addition to the ligand binding pocket also the native activation domain (activating function 2=AF2) allowing the fusion protein to function as a PPAR ligand dependent transcription factor. The GAL4 DBD will direct the chimeric protein to bind only to Gal4 enhancers (of which none existed in HEK293 cells). The reporter plasmid contained a Gal4 enhancer driving the expression of the firefly luciferase protein. After transfection, HEK293 cells expressed the GAL4-DBD-PPAR-LBD fusion protein. The fusion protein will in turn bind to the Gal4 enhancer controlling the luciferase expression, and do nothing in the absence of ligand. Upon addition to the cells of a PPAR ligand luciferase protein will be produced in amounts corresponding to the activation of the PPAR protein. The amount of luciferase protein is measured by light emission after addition of the appropriate substrate.

Cell Culture and Transfection

HEK293 cells were grown in DMEM+10% FCS. Cells were seeded in 96-well plates the day before transfection to give a confluency of 50-80% at transfection. A total of 0.8 µg DNA containing 0.64 µg pM1α/γLBD, 0.1 µg pCMVβGal, 0.08 µg pGL2(Gal4)$_5$ and 0.02 µg pADVANTAGE was transfected per well using FuGene transfection reagent according to the manufacturers instructions (Roche). Cells were allowed to express protein for 48 h followed by addition of compound.

Plasmids: Human PPAR-δ was obtained by PCR amplification using cDNA synthesized by reverse transcription of mRNA from human liver, adipose tissue and plancenta respectively. Amplified cDNAs were cloned into pCR2.1 and sequenced. The ligand binding domain (LBD) of each PPAR isoform was generated by PCR (PPARδ: aa 128-C-terminus) and fused to the DNA binding domain (DBD) of the yeast transcription factor GAL4 by sub-cloning fragments in frame into the vector pM1 (Sadowski et al. (1992), Gene 118, 137) generating the plasmids pM1αLBD, pM1γLBD and pM1δ. Ensuing fusions were verified by sequencing. The reporter was constructed by inserting an oligonucleotide encoding five repeats of the GAL4 recognition sequence (5×CGGAG-TACTGTCCTCCG(AG)) (Webster et al. (1988), Nucleic Acids Res. 16, 8192) into the vector pGL2 promotor (Promega) generating the plasmid pGL2(GAL4)$_5$. pCMVβ-Gal was purchased from Clontech and pADVANTAGE was purchased from Promega.

In Vitro Transactivation Assay

Compounds: All compounds were dissolved in DMSO and diluted 1:1000 upon addition to the cells. Compounds were tested in quadruple in concentrations ranging from 0.001 to 300 µM. Cells were treated with compound for 24 h followed by luciferase assay. Each compound was tested in at least two separate experiments.

Luciferase assay: Medium including test compound was aspirated and 100 µl PBS incl. 1 mM Mg++ and Ca++ were added to each well. The luciferase assay was performed using the LucLite kit according to the manufacturer's instructions (Packard Instruments). Light emission was quantified by counting on a Packard LumiCounter. To measure β-galactosidase activity 25 µl supernatant from each transfection lysate was transferred to a new microplate. β-Galactosidase assays were performed in the microwell plates using a kit from Promega and read in a Labsystems Ascent Multiscan reader. The β-galactosidase data were used to normalize (transfection efficiency, cell growth etc.) the luciferase data.

Statistical Methods

The activity of a compound is calculated as fold induction compared to an untreated sample. For each compound the efficacy (maximal activity) is given as a relative activity compared to Wy14,643 for PPARα, Rosiglitazone for PPARγ and Carbacyclin for PPARδ. The EC50 is the concentration giving 50% of maximal observed activity. EC50 values were calculated via non-linear regression using GraphPad PRISM 3.02 (GraphPad Software, San Diego, Calif.). The results were expressed as means±SD.

While the invention has been described and illustrated with reference to certain preferred embodiments thereof, those skilled in the art will appreciate that various changes, modifications, and substitutions can be made therein without departing from the spirit and scope of the present invention. For example, effective dosages other than the preferred dosages as set forth herein may be applicable as a consequence of variations in the responsiveness of the mammal being treated for PPAR-δ mediated disease(s). Likewise, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present invention. Accordingly, the invention is not to be limited as by the appended claims.

The features disclosed in the foregoing description and/or in the claims may both separately ans in any combination thereof be material for realising the invention in diverse forms thereof.

Preferred Features of the Invention:

1. A compound of the general formula (I):

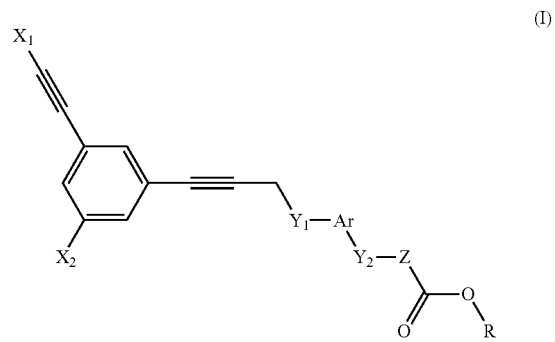

wherein $X_1$ is aryl, heteroaryl or heterocyclyl each of which is optionally substituted with one or more substituents selected from halogen, perhalomethyl, hydroxy, cyano, amino or carboxy; or $C_{1-6}$-alkyl, $C_{3-6}$-cycloalkyl, $C_{2-6}$-alkenyl, $C_{2-6}$-alkynyl, aryl, aralkyl, heteroaryl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkyl carbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted with one or more hydroxyl or halogens; or $X_1$ is aralkyl, heteroaralkyl or heterocyclyl-$C_{1-6}$-alkyl, each of which is optionally substituted with one or more substituents selected from halogen, perhalomethyl, hydroxy, cyano, amino or carboxy; or $C_{1-6}$-alkyl, $C_{3-6}$-cycloalkyl, $C_{2-6}$-alkenyl, $C_{2-6}$-alkynyl, aryl, aralkyl, heteroaryl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkyl carbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$- cycloalkylamino each of which is optionally substituted with one or more hydroxyl or halogens;

$X_2$ is hydrogen or halogen; or $X_2$ is aryl-$C_{2-6}$-alkynyl, heteroaryl-$C_{2-6}$-alkynyl, heterocyclyl-$C_{2-6}$-alkynyl, aryl-$C_{2-6}$-alkenyl, heteroaryl-$C_{2-6}$-alkenyl, heterocyclyl-$C_{2-6}$-alkenyl, aryl or heteroaryl each of which is optionally substituted with one or more substituents selected from halogen, perhalomethyl, hydroxy, cyano, amino or carboxy; or $C_{1-6}$-alkyl, $C_{3-6}$-cycloalkyl, $C_{2-6}$-alkenyl, $C_{2-6}$-alkynyl, aryl, aralkyl, heteroaryl, heteroaralkyl, heterocyclyl-$C_{1-6}$- alkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino each of which is optionally substituted with one or more hydroxyl or halogens;

Ar is arylene which is optionally substituted with one or more substituents selected from halogen, hydroxy or cyano; or $C_{1-6}$-alkyl, $C_{3-6}$-cycloalkyl, $C_{2-6}$-alkenyl, $C_{2-6}$-alkynyl, aryl, heteroaryl, aralkyl, heteroaralkyl, $C_{1-6}$-alkoxy, $C_{3-6}$-cycloalkoxy, aryloxy, aralkoxy, heteroaralkoxy, $C_{1-6}$-alkylthio, arylthio or $C_{3-6}$-cycloalkylthio each of which is optionally substituted with one or more halogens; or two of the substituents when placed in adjacent positions together with the atoms to which they are attached may form a five to eight member ring; and $Y_1$ is O or S; and $Y_2$ is O or S; and Z is —$(CH_2)_n$— wherein n is 1, 2 or 3; and R is hydrogen, $C_{1-6}$-alkyl, $C_{3-6}$-cycloalkyl, $C_{2-6}$-alkenyl, $C_{2-6}$-alkynyl, $C_{4-6}$-alkenynyl or aryl; or a pharmaceutically acceptable salt thereof, or a pharmaceutically acceptable solvate thereof, or any tautomeric forms, stereoisomers, mixture of stereoisomers including a racemic mixture, or polymorphs.

2. A compound according to clause 1 wherein $X_1$ is aryl, heteroaryl or heterocyclyl each of which is optionally substituted with one or more substituents selected from halogen, perhalomethyl, hydroxy or carboxy; or $C_{1-6}$-alkyl, $C_{3-6}$-cycloalkyl, aryl, aralkyl, heteroaryl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted with one or more halogens.

3. A compound according to clause 2 wherein $X_1$ is aryl, heteroaryl or heterocyclyl each of which is optionally substituted with one or more substituents selected from halogen, perhalomethyl or hydroxy; or $C_{1-6}$-alkyl, $C_{3-6}$-cycloalkyl, aryl, aralkyl, $C_{1-6}$-alkoxy, $C_{1-6}$-alkylsulfonyl or arylsulfonyl, each of which is optionally substituted with one or more halogens.

4. A compound according to clause 3 wherein $X_1$ is aryl, heteroaryl or heterocyclyl each of which is optionally substituted with one or more substituents selected from halogen, perhalomethyl or hydroxy; or $C_{1-6}$-alkyl, aryl, or $C_{1-6}$-alkylsulfonyl, each of which is optionally substituted with one or more halogens.

5. A compound according to clause 2 wherein $X_1$ is aryl, which is optionally substituted with one or more substituents selected from halogen, perhalomethyl, hydroxy or carboxy; or $C_{1-6}$-alkyl, $C_{3-6}$-cycloalkyl, aryl, aralkyl, heteroaryl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted with one or more halogens.

6. A compound according to clause 5 wherein $X_1$ is aryl, which is optionally substituted with one or more substituents selected from halogen, perhalomethyl or hydroxy; or $C_{1-6}$-alkyl, $C_{3-6}$-cycloalkyl, aryl, aralkyl, $C_{1-6}$-alkoxy, $C_{1-6}$-alkylsulfonyl or arylsulfonyl, each of which is optionally substituted with one or more halogens.

7. A compound according to clause 1 wherein $X_1$ aralkyl, heteroaralkyl or heterocyclyl-$C_{1-6}$-alkyl each of which is optionally substituted with one or more substituents selected from halogen, perhalomethyl, hydroxy or carboxy; or $C_{1-6}$-alkyl, $C_{3-6}$-cycloalkyl, aryl, aralkyl, heteroaryl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted with one or more halogens.

8. A compound according clause 7 wherein $X_1$ is aralkyl, heteroaralkyl or heterocyclyl-$C_{1-6}$-alkyl each of which is optionally substituted with one or more substituents selected from halogen, perhalomethyl or hydroxy; or $C_{1-6}$-alkyl, $C_{3-6}$-cycloalkyl, aryl, aralkyl, $C_{1-6}$-alkoxy, $C_{1-6}$-alkylsulfonyl or arylsulfonyl, each of which is optionally substituted with one or more halogens.

9. A compound according to clause 7 wherein $X_1$ is heterocyclyl-$C_{1-6}$-alkyl, which is optionally substituted with one or more substituents selected from halogen, perhalomethyl, hydroxy or carboxy; or $C_{1-6}$-alkyl, $C_{3-6}$-cycloalkyl, aryl, aralkyl, heteroaryl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted with one or more halogens.

10. A compound according to clause 9 wherein $X_1$ is heterocyclyl-$C_{1-6}$-alkyl, which is optionally substituted with one or more substituents selected from halogen, perhalomethyl or hydroxy; or $C_{1-6}$-alkyl, $C_{3-6}$-cycloalkyl, aryl, aralkyl, $C_{1-6}$-alkoxy, $C_{1-6}$-alkylsulfonyl or arylsulfonyl, each of which is optionally substituted with one or more halogens.

11. A compound according to any one of the preceding clauses wherein $X_2$ is halogen.

12. A compound according to any one of the clauses 1-10 wherein $X_2$ is aryl-$C_{2-6}$-alkynyl, heteroaryl-$C_{2-6}$-alkynyl, heterocyclyl-$C_{2-6}$-alkynyl, aryl-$C_{2-6}$-alkenyl, heteroaryl-$C_{2-6}$- alkenyl, heterocyclyl-$C_{2-6}$-alkenyl, aryl or heteroaryl each of which is optionally substituted with one or more substituents selected from
halogen, perhalomethyl, hydroxy or carboxy; or
$C_{1-6}$-alkyl, $C_{3-6}$-cycloalkyl, aryl, aralkyl, heteroaryl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted with one or more halogens.

13. A compound according to clause 12 wherein $X_2$ is aryl-$C_{2-6}$-alkynyl, heteroaryl-$C_{2-6}$-alkynyl, heterocyclyl-$C_{2-6}$-alkynyl, aryl-$C_{2-6}$-alkenyl, heteroaryl-$C_{2-6}$-alkenyl, heterocyclyl-$C_{2-6}$-alkenyl, aryl or heteroaryl each of which is optionally substituted with one or more substituents selected from
halogen, perhalomethyl or hydroxy; or
$C_{1-6}$-alkyl, $C_{3-6}$-cycloalkyl, aryl, aralkyl, $C_{1-6}$-alkoxy, $C_{1-6}$-alkylsulfonyl or arylsulfonyl, each of which is optionally substituted with one or more halogens.

14. A compound according to clause 12 wherein $X_2$ is aryl-$C_{2-6}$-alkynyl, which is optionally substituted with one or more substituents selected from
halogen, perhalomethyl, hydroxy or carboxy; or
$C_{1-6}$-alkyl, $C_{3-6}$-cycloalkyl, aryl, aralkyl, heteroaryl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted with one or more halogens.

15. A compound according to clause 14 wherein $X_2$ is aryl-$C_{2-6}$-alkynyl, which is optionally substituted with one or more substituents selected from
halogen, perhalomethyl or hydroxy; or
$C_{1-6}$-alkyl, $C_{3-6}$-cycloalkyl, aryl, aralkyl, $C_{1-6}$-alkoxy, $C_{1-6}$-alkylsulfonyl or arylsulfonyl, each of which is optionally substituted with one or more halogens.

16. A compound according to clause 12 wherein $X_2$ is heterocyclyl-$C_{2-6}$-alkynyl, which is optionally substituted with one or more substituents selected from
halogen, perhalomethyl, hydroxy or carboxy; or
$C_{1-6}$-alkyl, $C_{3-6}$-cycloalkyl, aryl, aralkyl, heteroaryl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted with one or more halogens.

17. A compound according to clause 16 wherein $X_2$ is heterocyclyl-$C_{2-6}$-alkynyl, which is optionally substituted with one or more substituents selected from
halogen, perhalomethyl or hydroxy; or
$C_{1-6}$-alkyl, $C_{3-6}$-cycloalkyl, aryl, aralkyl, $C_{1-6}$-alkoxy, $C_{1-6}$-alkylsulfonyl or arylsulfonyl, each of which is optionally substituted with one or more halogens.

18. A compound according to any one of the preceding clauses wherein Ar is arylene which is optionally substituted with one or more substituents selected from
halogen; or
$C_{1-6}$-alkyl, $C_{1-6}$-alkoxy, aryloxy or aralkoxy each of which is optionally substituted with one or more halogens; or
two of the substituents when placed in adjacent positions together with the atoms to which they are attached form a five membered carbon cycle.

19. A compound according to clause 18 wherein Ar is phenylene which is optionally substituted with one or more substituents selected from
halogen; or
$C_{1-6}$-alkyl, $C_{1-6}$-alkoxy, aryloxy or aralkoxy each of which is optionally substituted with one or more halogens; or
two of the substituents when placed in adjacent positions together with the atoms to which they are attached form a five membered carbon cycle.

20. A compound according to clause 19 wherein Ar is phenylene, optionally substituted with one or more of $C_{1-6}$-alkyl.

21. A compound according to any one of the preceding clauses wherein $Y_1$ is O.

22. A compound according to any one of the preceding clauses wherein $Y_2$ is O.

23. A compound according to any one of the preceding clauses wherein n is 1.

24. A compound according to any one of the preceding clauses wherein R is hydrogen or $C_{1-6}$-alkyl.

25. A compound according to any one of the preceding clauses wherein R is hydrogen.

26. A compound according to any one of the preceding clauses which is:
{4-[3-(3-Bromo-5-phenylethynyl-phenyl)-prop-2-ynyloxy]-phenoxy}-acetic acid;
{4-[3-(3,5-Bis-phenylethynyl-phenyl)-prop-2-ynyloxy]-phenoxy}-acetic acid;
(4-{3-[3-Bromo-5-(3-piperidin-1-yl-prop-1-ynyl)-phenyl]-prop-2-ynyloxy}-2-methyl-phenoxy)-acetic acid;
(2-Methyl-4-{3-[3-(3-piperidin-1-yl-prop-1-ynyl)-5-(4-trifluoromethyl-phenylethynyl)-phenyl]-prop-2-ynyloxy}-phenoxy)-acetic acid;
(4-{3-[3,5-Bis-(3-piperidin-1-yl-prop-1-ynyl)-phenyl]-prop-2-ynyloxy}-2-methyl-phenoxy)-acetic acid;
(4-{3-[3-Bromo-5-(3-morpholin-4-yl-prop-1-ynyl)-phenyl]-prop-2-ynyloxy}-2-methyl-phenoxy)-acetic acid;
(2-Methyl-4-{3-[3-(3-morpholin-4-yl-prop-1-ynyl)-5-(4-trifluoromethyl-phenylethynyl)-phenyl]-prop-2-ynyloxy}-phenoxy)-acetic acid;
(2-Methyl-4-{3-[3-(3-morpholin-4-yl-prop-1-ynyl)-5-phenylethynyl-phenyl]-prop-2-ynyloxy}-phenoxy)-acetic acid;
(4-{3-[3-(4-Chloro-phenylethynyl)-5-(3-morpholin-4-yl-prop-1-ynyl)-phenyl]-prop-2-ynyloxy}-2-methyl-phenoxy)-acetic acid;
(4-{3-[3-(4-Methanesulfonyl-phenylethynyl)-5-(3-morpholin-4-yl-prop-1-ynyl)-phenyl]-prop-2-ynyloxy}-2-methyl-phenoxy)-acetic acid;
(4-{3-[3-Bromo-5-(4-trifluoromethyl-phenylethynyl)-phenyl]-prop-2-ynyloxy}-2-methyl-phenoxy)-acetic acid; or
a salt thereof with a pharmaceutically acceptable acid or base, or any optical isomer or mixture of optical isomers, including a racemic mixture, or any tautomeric forms.

27. A compound according to any one of the preceding clauses, which is a PPARδ agonist.

28. A compound according to clause 27, which is a selective PPARδ agonist.

29. The use of a compound according to any one of the preceding clauses as a pharmaceutical composition.

30. A pharmaceutical composition comprising, as an active ingredient, at least one compound according to any one of the clauses 1-28 together with one or more pharmaceutically acceptable carriers or excipients.

31. A pharmaceutical composition according to clause 30 in unit dosage form, comprising from about 0.05 mg to about 1000 mg, preferably from about 0.1 to about 500 mg of and especially preferred from about 0.5 mg to about 200 mg per day of compound according to any one of the clauses 1-28.

32. A pharmaceutical composition for the treatment and/or prevention of conditions mediated by nuclear receptors, in particular PPARδ, the composition comprising a compound according to any one of the clauses 1-28 together with one or more pharmaceutically acceptable carriers or excipients.

33. A pharmaceutical composition for the treatment and/or prevention of type I diabetes, type 11 diabetes, impaired glucose tolerance, insulin resistance or obesity comprising a compound according to any of the clauses 1-28 together with one or more pharmaceutically acceptable carriers or excipients.

34. A pharmaceutical composition according to any one of the clauses 30-33 for oral, nasal, transdermal, pulmonal or parenteral administration.

35. Use of a compound according to any one of the clauses 1-28 for the preparation of a pharmaceutical composition for the treatment and/or prevention of conditions mediated by nuclear receptors, in particular the PPARδ.

36. Use of a compound according to any one of the clauses 1-28 for the preparation of a pharmaceutical composition for the treatment and/or prevention of Type 1 diabetes, Type 2 diabetes, dyslipidemia, syndrome X (including the metabolic syndrome, i.e. impaired glucose tolerance, insulin resistance, hypertrigyceridaemia and/or obesity), cardiovascular diseases (including atherosclerosis) and hypercholesteremia.

37. A method for the treatment and/or prevention of conditions mediated by nuclear receptors, in particular the PPARδ, the method comprising administering to a subject in need thereof an effective amount of a compound according to any one of the clauses 1-28 or a pharmaceutical composition comprising the same.

38. A method for the treatment and/or prevention of type I diabetes, type II diabetes, impaired glucose tolerance, insulin resistance or obesity, the method comprising administering to a subject in need thereof an effective amount of a compound according to any one of the clauses 1-28 or of a pharmaceutical composition comprising the same.

39. The method according to clauses 37 or 38 wherein the effective amount of the compound according to any one of the clauses 1-28 is in the range of from about 0.05 mg to about 1000 mg, preferably from about 0.1 to about 500 mg of and especially preferred from about 0.5 mg to about 200 mg per day.

The invention claimed is:

1. A compound of formula (I) or a pharmaceutically acceptable salt thereof:

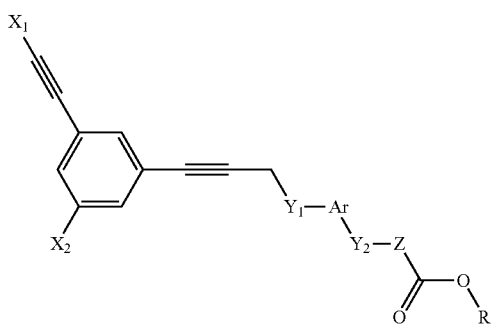

(I)

wherein $X_1$ is aryl, heteroaryl or heterocyclyl each of which is optionally substituted with one or more substituents, where said substituents independently are:

halogen, perhalomethyl, hydroxy, cyano, amino or carboxy; or $C_{1-6}$-alkyl, $C_{3-6}$-cycloalkyl, $C_{2-6}$-alkenyl, $C_{2-6}$-alkynyl, aryl, aralkyl, heteroaryl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkyl-amido, arylamido, $C_{1-6}$-alkylaminocarbonyl, $C_{1-6}$-alkylamino, $C_{1-6}$-dialkylamino or $C_{3-6}$-cycloalkylamino, each of which is optionally substituted independently with one or more hydroxyl groups or halogens; or $X_1$ is aralkyl, heteroaralkyl or heterocyclyl-$C_{1-6}$-alkyl, each of which is optionally substituted with one or more substituents, where said substituents independently are:

halogen, perhalomethyl, hydroxy, cyano, amino or carboxy; or $C_{1-6}$-alkyl, $C_{3-6}$-cycloalkyl, $C_{2-6}$-alkenyl, $C_{2-6}$-alkynyl, aryl, aralkyl, heteroaryl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$cycloalkylthio, $C_{1-6}$-alkylcarbonyl, arylcarbonyl, $C_{1-6}$-alkylsulfonyl, arylsulfonyl, $C_{1-6}$-alkyl-amido, arylamido, $C_{1-6}$-alkylaminocarbonyl, $C_{1-6}$-alkylamino, $C_{1-6}$-dialkylamino or $C_{3-6}$-cycloalkylamino each of which is optionally substituted independently with one or more hydroxyl groups or halogens;

$X_2$ is hydrogen or halogen; or $X_2$ is aryl-$C_{2-6}$-alkynyl, heteroaryl-$C_{2-6}$-alkynyl, heterocyclyl-$C_{2-6}$-alkynyl, aryl-$C_{2-6}$-alkenyl, heteroaryl-$C_{2-6}$-alkenyl, heterocyclyl-$C_{2-6}$-alkenyl, aryl or heteroaryl each of which is optionally substituted with one or more substiuents, where said substituents independently are:

halogen, perhalomethyl, hydroxy, cyano, amino or carboxy; or $C_{1-6}$-alkyl, $C_{3-6}$-cycloalkyl, $C_{2-6}$-alkenyl, $C_{2-6}$-alkynyl, aryl, aralkyl, heteroaryl, heteroaralkyl, heterocyclyl-$C_{1-6}$-alkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-di-alkylamino or $C_{3-6}$-cycloalkylamino, each of which is optionally substituted independently with one or more hydroxyl groups or halogens;

Ar is arylene which is optionally substituted with one or more substituents, where said substituents independently are:

halogen, hydroxy or cyano; or $C_{1-6}$-alkyl, $C_{3-6}$-cycloalkyl, $C_{2-6}$-alkenyl, $C_{2-6}$-alkynyl, aryl, heteroaryl, aralkyl, heteroaralkyl, $C_{1-6}$-alkoxy, $C_{3-6}$-cycloalkoxy, aryloxy, aralkoxy, heteroaralkoxy, $C_{1-6}$-alkylthio, arylthio or $C_{3-6}$-cycloalkylthio, each of which is optionally substituted with one or more halogens; or two of the substituents when placed in adjacent positions together with the atoms to which they are attached may form a five to eight member ring;

$Y_1$ is O or S;

$Y_2$ is O or S;

Z is —$(CH_2)_n$— wherein n is 1, 2 or 3; and

R is hydrogen;

or a hydrate of any of the foregoing.

2. The compound according to claim 1, wherein $X_1$ is aryl, heteroaryl or heterocyclyl each of which is optionally substituted with one or more substituents, where said substituents independently are:

halogen, perhalomethyl or hydroxy; or $C_{1-6}$-alkyl, $C_{3-6}$-cycloalkyl, aryl, aralkyl, $C_{1-6}$-alkoxy, $C_{1-6}$-alkylsulfonyl or arylsulfonyl, each of which is optionally substituted with one or more halogens.

3. The compound according claim 1 wherein $X_1$ is aralkyl, heteroaralkyl or heterocyclyl-$C_{1-6}$-alkyl each of which is optionally substituted with one or more substituents, where said substituents independently are:

halogen, perhalomethyl or hydroxy; or $C_{1-6}$-alkyl, $C_{3-6}$-cycloalkyl, aryl, aralkyl, $C_{1-6}$-alkoxy, $C_{1-6}$-alkylsulfonyl or arylsulfonyl, each of which is optionally substituted with one or more halogens.

4. The compound according to claim 1 wherein $X_2$ is halogen.

5. The compound according to claim 1 wherein $X_2$ is aryl-$C_{2-6}$-alkynyl, heteroaryl-$C_{2-6}$-alkynyl, heterocyclyl-$C_{2-6}$-alkynyl, aryl-$C_{2-6}$-alkenyl, heteroaryl-$C_{2-6}$-alkenyl, heterocyclyl-$C_{2-6}$-alkenyl, aryl or heteroaryl each of which is optionally substituted with one or more substituents, where said substituents independently are:

halogen, perhalomethyl or hydroxy; or $C_{1-6}$-alkyl, $C_{3-6}$-cycloalkyl, aryl, aralkyl, $C_{1-6}$-alkoxy, $C_{1-6}$-alkylsulfonyl or arylsulfonyl, each of which is optionally substituted with one or more halogens.

6. The compound according to claim 5 wherein $X_2$ is heterocyclyl-$C_{2-6}$-alkynyl, which is optionally substituted with one or more substituents, where said substituents independently are:

halogen, perhalomethyl or hydroxy; or $C_{1-6}$-alkyl, $C_{3-6}$-cycloalkyl, aryl, aralkyl, $C_{1-6}$-alkoxy, $C_{1-6}$-alkylsulfonyl or arylsulfonyl, each of which is optionally substituted with one or more halogens.

7. The compound according to claim 1 wherein Ar is phenylene which is optionally substituted with one or more substituents, where said substituents independently are:

halogen; or $C_{1-6}$-alkyl, $C_{1-6}$-alkoxy, aryloxy or aralkoxy each of which is optionally substituted with one or more halogens; or two of the substituents when placed in adjacent positions together with the atoms to which they are attached form a five-membered carbon cycle.

8. The compound according claim 1 wherein $X_1$ is heterocyclyl-$C_{1-6}$-alkyl, which is optionally substituted with one or more substituents, where said substituents independently are:

halogen, perhalomethyl or hydroxy; or $C_{1-6}$-alkyl, $C_{3-6}$-cycloalkyl, aryl, aralkyl, $C_{1-6}$-alkoxy, $C_{1-6}$-alkylsulfonyl or arylsulfonyl, each of which is optionally substituted with one or more halogens.

9. The compound according to claim 8 wherein $Y_1$ is O.

10. The compound according to claim 9 wherein $Y_2$ is O.

11. The compound according to claim 10 wherein n is 1.

12. A compound, which is a compound selected from the group consisting of:

{4-[3-(3-Bromo-5-phenylethynyl-phenyl)-prop-2-ynyloxy]-phenoxy}-acetic acid;

{4-[3-(3,5-Bis-phenylethynyl-phenyl)-prop-2-ynyloxy]-phenoxy}-acetic acid;

(4-{3-[3-Bromo-5-(3-piperidin-1-yl-prop-1-ynyl)-phenyl]-prop-2-ynyloxy}-2-methyl-phenoxy)-acetic acid;

(2-Methyl-4-{3-[3-(3-piperidin-1-yl-prop-1-ynyl)-5-(4-trifluoromethyl-phenylethynyl)-phenyl]-prop -2-ynyloxy}-phenoxy)-acetic acid;

(4-{3-[3,5-Bis-(3-piperidin-1-yl-prop-1-ynyl)-phenyl]-prop-2-ynyloxy}-2-methyl-phenoxy)-acetic acid;

(4-{3-[3-Bromo-5-(3-morpholin-4-yl-prop-1-ynyl)-phenyl]-prop-2-ynyloxy}-2-methyl-phenoxy)-acetic acid;

(2-Methyl-4-{3-[3-(3-morpholin-4-yl-prop-1-ynyl)-5-(4-trifluoromethyl-phenylethynyl)-phenyl]-prop -2-ynyloxy}-phenoxy)-acetic acid;

(2-Methyl-4-{3-[3-(3-morpholin-4-yl-prop-1-ynyl)-5-phenylethynyl-phenyl]-prop-2-ynyloxy}-phenoxy)-acetic acid;

(4-{3-[3-(4-Chloro-phenylethynyl)-5-(3-morpholin-4-yl-prop-1-ynyl)-phenyl]-prop-2-ynyloxy}-2-methyl-phenoxy)-acetic acid;

(4-{3-[3-(4-Methanesulfonyl-phenylethynyl)-5-(3-morpholin-4-yl-prop-1-ynyl)-phenyl]-prop-2-ynyloxy }-2-methyl-phenoxy)-acetic acid; and (4-{3-[3-Bromo-5-(4-trifluoromethyl-phenylethynyl)-phenyl]-prop-2-ynyloxy}-2-methyl-phenoxy)-acetic acid;

or a pharmaceutically acceptable salt thereof, or a hydrate of any of the foregoing.

13. A pharmaceutical composition comprising a compound according to claim 1 and a pharmaceutically acceptable carrier or excipient.

14. A pharmaceutical composition comprising a compound according to claim 12 and a pharmaceutically acceptable carrier or excipient.

* * * * *